(12) United States Patent
Osterfeld et al.

(10) Patent No.: US 9,151,763 B2
(45) Date of Patent: Oct. 6, 2015

(54) SYSTEMS AND METHODS FOR HIGH-THROUGHPUT DETECTION OF AN ANALYTE IN A SAMPLE

(75) Inventors: Sebastian J. Osterfeld, Mountain View, CA (US); Shan X. Wang, Portola Valley, CA (US)

(73) Assignee: MagArray, Inc., Milpitas, CA (US)

( * ) Notice: Subject to any disclaimer, the term of this patent is extended or adjusted under 35 U.S.C. 154(b) by 17 days.

(21) Appl. No.: 13/416,928

(22) Filed: Mar. 9, 2012

(65) Prior Publication Data

US 2012/0231960 A1    Sep. 13, 2012

Related U.S. Application Data

(60) Provisional application No. 61/450,655, filed on Mar. 9, 2011.

(51) Int. Cl.

| G01N 27/00 | (2006.01) |
|---|---|
| G01N 33/58 | (2006.01) |
| C40B 60/12 | (2006.01) |
| B01L 3/00 | (2006.01) |

(Continued)

(52) U.S. Cl.
CPC ............ G01N 33/587 (2013.01); B01L 3/5085 (2013.01); B01L 9/523 (2013.01); B82Y 15/00 (2013.01); B82Y 30/00 (2013.01); C40B 60/12 (2013.01); G01N 27/3276 (2013.01); G01N 27/745 (2013.01); G01N 35/0098 (2013.01); G01R 33/0094 (2013.01); G01R 33/1269 (2013.01); *B01J 2219/00317* (2013.01); *B01J 2219/00655* (2013.01); *B01J 2219/00662* (2013.01); *B01L 2300/0829* (2013.01); *B82Y 10/00* (2013.01); *G01N 35/026* (2013.01); *Y10S 977/773* (2013.01); *Y10S 977/92* (2013.01)

(58) Field of Classification Search
CPC .................................................. G01N 27/9033
USPC .................................................. 422/503, 502
See application file for complete search history.

(56) References Cited

U.S. PATENT DOCUMENTS

| 5,981,297 A | 11/1999 | Baselt |
|---|---|---|
| 6,323,634 B1 | 11/2001 | Naakagawa et al. |

(Continued)

FOREIGN PATENT DOCUMENTS

| WO | 01/014591 | 3/2001 |
|---|---|---|
| WO | 01/057506 | 8/2001 |

(Continued)

OTHER PUBLICATIONS

Han; et al., "CMOS integrated DNA microarray based on GMR sensors", IEDM '06 (2006), 4 pages.

(Continued)

*Primary Examiner* — Natalia Levkovich
(74) *Attorney, Agent, or Firm* — Rudy J. Ng; Bret E. Field; Bozicevic, Field & Francis LLP

(57) ABSTRACT

Provided are high-throughput detection systems. The systems include a magnetic sensor device, a magnetic field source and a reservoir plate that includes a plurality of fluid reservoirs. The magnetic sensor device includes a support with two or more elongated regions each having a magnetic sensor array disposed at a distal end. Also provided are methods in which the subject high-throughput detection systems find use.

19 Claims, 4 Drawing Sheets

(51) Int. Cl.
| | |
|---|---|
| *B82Y 15/00* | (2011.01) |
| *B82Y 30/00* | (2011.01) |
| *G01N 27/327* | (2006.01) |
| *G01R 33/12* | (2006.01) |
| *G01N 27/74* | (2006.01) |
| *G01N 35/00* | (2006.01) |
| *G01R 33/00* | (2006.01) |
| *B01L 9/00* | (2006.01) |
| *B82Y 10/00* | (2011.01) |
| *G01N 35/02* | (2006.01) |

(56) References Cited

U.S. PATENT DOCUMENTS

| | | | |
|---|---|---|---|
| 6,582,921 B2 | 6/2003 | Mirkin et al. | |
| 6,623,983 B1 | 9/2003 | Terstappen et al. | |
| 6,679,130 B2 | 1/2004 | Hajduk et al. | |
| 7,906,345 B2 | 3/2011 | Wang et al. | |
| 2002/0014408 A1 | 2/2002 | Schroeder | |
| 2002/0060565 A1 | 5/2002 | Tondra | |
| 2003/0204133 A1 | 10/2003 | Harjunmaa et al. | |
| 2004/0002121 A1 | 1/2004 | Regan et al. | |
| 2004/0002169 A1 | 1/2004 | Kraus et al. | |
| 2004/0086424 A1* | 5/2004 | Schembri | 422/58 |
| 2005/0025969 A1 | 2/2005 | Berning et al. | |
| 2005/0100930 A1 | 5/2005 | Wang et al. | |
| 2005/0258821 A1 | 11/2005 | Wang et al. | |
| 2006/0051247 A1 | 3/2006 | Micklash et al. | |
| 2006/0269385 A1 | 11/2006 | Zobel et al. | |
| 2007/0003994 A1 | 1/2007 | Simpson et al. | |
| 2007/0122898 A1 | 5/2007 | Sharma | |
| 2007/0166835 A1 | 7/2007 | Bobrow et al. | |
| 2007/0178504 A1 | 8/2007 | Colpitts et al. | |
| 2007/0237673 A1 | 10/2007 | Ikeda et al. | |
| 2008/0024117 A1 | 1/2008 | Hong et al. | |
| 2008/0160622 A1 | 7/2008 | Su et al. | |
| 2009/0005495 A1 | 1/2009 | Ban et al. | |
| 2009/0104707 A1 | 4/2009 | Wang et al. | |
| 2010/0188075 A1 | 7/2010 | Litvinov et al. | |
| 2011/0027901 A1 | 2/2011 | Gaster et al. | |

FOREIGN PATENT DOCUMENTS

| | | |
|---|---|---|
| WO | 03/031977 | 4/2003 |
| WO | 03/054523 | 7/2003 |
| WO | 03/081202 | 10/2003 |
| WO | 2005/059929 A2 | 6/2005 |
| WO | 2008/001261 | 1/2008 |

OTHER PUBLICATIONS

Baselt, D.R., et al.; "A Biosensor Based on Magnetoresistance Technology," Biosensors and Bioelectronics, Oct. 1998, 13(7-8):731-739.
Bozorth, R.M., "Ferromagnetism," D. Van Nostrand Company, Inc. (1951), pp. 190-209.
Ferreira H. A. et al. "Biodetection using magnetically labeled biomolecules and arrays of spin valve sensors (invited)", Journal of Applied Physics, May 15, 2003, 93(10):7281-7286, XP012058127, ISSN: 0021-8979.
Ferreira H. A. et al., "Detection of biomolecular recognition using nanometer-sized magnetic labels and spin-valve sensors", Digest of Intermag 2003, IEEE International Magnetics Conference, Mar. 28, 2003, pp. EC-4, XP010665265, ISBN: 0-7803-7647-1.
Freitas P. P. et al., "Magnetoresistive biochips", Europhysics News, Nov. 2003, 34(6):224-226, XP002429397, ISSN: 0531-7479.
Graham D. L. et al., "High sensitivity detection of molecular recognition using magnetically labelled biomolecules and magnetoresistive sensors", Biosensors and Bioelectronics, Apr. 1, 2003, 18(4):483-488, XP002429396.
Graham, D. L., et al.; "Single Magnetic Microsphere Placement and Detection on-chip Using Current Line Designs with Integrated Spin Valve Sensors: Biotechnological Applications" J. Appl. Phys. (200.
Guanxiong Li et al., "Analytical and micromagnetic modeling for detection of a single magnetic microbead or nanobead by spin valve sensors", IEEE Transactions on Magnetics, 39(5):3313-3315, XP011101285, ISSN:0018-9464.
Han; et al., "A High-Density Magnetoresistive Biosensor Array with Drift-Compensation Mechanism", 2007 IEEE International Solid-State Circuits Conference (2007), Session 8, pp. 168-169, 594.
Han; et al., "CMOS Integrated DNA Microarray Based on GMR Sensors", Electron Devices Meeting (2006), pp. 1-4.
Lagae L. et al., "On-chip manipulation and magnetization assessment of magnetic bead ensembles by integrated spin-valve sensors", Journal of Applied Physics, May 15, 2002, 91(10):7445-7447, XP012054843, ISSN: 0021-8979.
Li, G., et al.; "Analytical and Micromagnetic Modeling for Detection of a Single Magnetic Microbead or Nanobead by Spin Valve Sensors;" IEEE Trans. Magn. (2003), 39(5):3313-3315.
Li, G. et al.; "Detection of Single Micron-Sized Magnetic Bead and Magnetic Nanoparticles Using Spin Valve Sensors for Biological Applications;" J. Appl. Phys. (2003), 93(10):7557-7559.
Li; et al., "Spin valve sensors for ultrasensitive detection of superparamagnetic nanoparticles for biological applications", Sensors and Actuators (2006), 126(1):98-106.
Miller, M. M., et al.; "A DNA Array Sensor Utilizing Magnetic Microbeads and Magnetoelectronic Detection;" Journal of Magnetism and Magnetic Materials (2001), 225:138-144.
Murray, et al., "New Aspects of Nanocrystal Research", MRS Bulletin (2001), vol. 26 (12): pp. 985-991.
Parkin, S.S.P., et al.; Exchange-Biased Magnetic Tunnel Junctions and Applications to Nonvolatile Magnetic Random Access Memory (Invited); J. Appl. Phys. (1999), 85(8):5828-5833.
Parkin, S. S. P., et al. "Oscillations in Exchange Coupling and Magnetoresistance in Metallic Superlattice Structures: CoJRu, ColCr, and FelCr;" Phys. Rev. Lett. (1990), 64(19):2304-7.
Schena; et al., "Microarray Biochip Technology", Eaton Publishing, (2000), pp. 1-18.
Sellmyer, D.J., et al; "Handbook of Thin Film Materials;" Edited by: Nalwa, H.S., Stanford Scientific Corporation; Academic Press (2002), 5:337-374.
Slonczewski, John C., et al.; "Micromagnetics of Laminated Permalloy Films;" IEEE Trans. Magn. (1998), 24(3):2045-2054.
Sun, S., et al.; "Polymer Mediated Self-Assembly of Magnetic Nanoparticles;" J. Am. Chem. Soc. (2002), 124(12):2884-2885.
Sun, S., et al.; "Monodisperse MFe2O4 (M = Fe, Co, Mn) Nanoparticles;" IBM T. J. Watson Research Center, Yorktown Heights, NY; pp. 1-24.
Sun, S.; et al.; "Synthesis of Monodisperse Cobalt Nanocrystals and their Assembly into Magnetic Superlattices;" J. Appl. Phys. (1999), 85(8):4325-30.
Tehrani, S., et al.; "Recent Developments in Magnetic Tunnel Junction MRAM;" IEEE Trans. Magn. (2000), 36(5):2752-2757.
Thorsen, T., et al., "Microfluidic Large-Scale Integration;" Science (2002), 298:580-584.
Trademark Electronic Search System (Tess) for "MAGARRAY;" http://tess2.uspto.~ov/bin/showfield?f=doc&state=ut16qp.2.10;9 11 Mar. 2004,3 pages.
Van de Veerdonk, R.J.M., et al., "Current Distribution Effects in Magnetoresistive Tunnel Junctions;" Appl. Phys. Lett. (1997), 71 (19):2839-2841.
Wang S. X. et al., "Design and fabrication of bio-magnetic sensors and magnetic nanobead labels for dna detection and identification", Digest of Intermag 2003, IEEE International Magnetics Conference, Mar. 28, 2003, pp. EC-1, XP01066526, ISBN: 0-7803-7647-1.
Xu; et al., "Giant magnetoresistive biochip for DNA detection and HPV genotyping", Biosensors and Bioelectronics (2008), 24(1):99-103.

* cited by examiner

SYSTEMS AND METHODS FOR HIGH-THROUGHPUT DETECTION OF AN ANALYTE IN A SAMPLE

CROSS-REFERENCE TO RELATED APPLICATIONS

Pursuant to 35 U.S.C. §119(e), this application claims priority to the filing date of U.S. Provisional Patent Application Ser. No. 61/450,655 filed on Mar. 9, 2011, the disclosure of which application is herein incorporated by reference.

REFERENCE TO GOVERNMENT SUPPORT

This invention was made with Government support under Grant No. N44CM-2009-00011 from the National Cancer Institute. The government has certain rights in this invention.

INTRODUCTION

High-throughput detection is a method for scientific experimentation used, for example, in clinical diagnostics, drug discovery and relevant fields of biology and chemistry. High-throughput detection allows a researcher to quickly conduct many chemical, genetic, proteomic, or pharmacological tests. For instance, using a high-throughput detection process, one can rapidly identify active compounds, antibodies or genes which modulate a particular biomolecular pathway. The results of these experiments provide starting points for drug design and for understanding the interaction or role of a particular biochemical process in biology.

SUMMARY

Provided are high-throughput detection systems. The systems include a magnetic sensor device, a magnetic field source and a reservoir plate that includes a plurality of fluid reservoirs. The magnetic sensor device includes a support with two or more elongated regions each having a magnetic sensor array disposed at a distal end. Also provided are methods in which the subject high-throughput detection systems find use.

Embodiments of the present disclosure include a high-throughput detection system. The system includes: (a) a magnetic sensor device; (b) a magnetic field source; and (c) a reservoir plate having a plurality of fluid reservoirs, where the system is configured to position the magnetic sensor arrays in sequential sets of the fluid reservoirs. The magnetic sensor device includes a support with two or more elongated regions each having a magnetic sensor array disposed at a distal end.

In some embodiments of the system, each magnetic sensor array includes one or more magnetic sensors having an analyte-specific probe bound to a surface of the magnetic sensor.

In some embodiments, the system includes a first reservoir plate actuator configured to move the reservoir plate into an operative relationship with the magnetic sensor device such that the distal ends of the elongated regions of the magnetic sensor device are each positioned in separate fluid reservoirs.

In some embodiments, the system includes a second reservoir plate actuator configured to move the reservoir plate along at least one axis coplanar with the reservoir plate.

In some embodiments, the system includes a magnetic sensor device actuator configured to move the magnetic sensor device into an operative relationship with the magnetic field source.

In some embodiments, the system includes a processor configured to obtain a real-time analyte-specific signal from the magnetic sensor array.

In some embodiments of the system, the processor is configured to obtain the real-time analyte-specific signal from the magnetic sensor array as a magnetically-labeled analyte in a sample binds to an analyte-specific probe or as a magnetic label binds to an analyte/analyte-specific probe complex.

Embodiments of the present disclosure include a high-throughput detection system that includes: (a) a magnetic field source; and (b) a first reservoir plate actuator configured to position a reservoir plate having a plurality of fluid reservoirs into an operative relationship with a magnetic sensor device comprising two or more magnetic sensor arrays, where the system is configured to position the two or more magnetic sensor arrays in sequential sets of the fluid reservoirs.

In some embodiments, the system includes a second reservoir plate actuator configured to move the reservoir plate along at least one axis coplanar with the reservoir plate.

In some embodiments, the system includes a magnetic sensor device actuator configured to move the magnetic sensor device into an operative relationship with the magnetic field source.

In some embodiments, the system includes a processor configured to obtain a real-time analyte-specific signal from the magnetic sensor arrays.

Embodiments of the present disclosure include a magnetic sensor device that includes a support with two or more elongated regions each having a magnetic sensor array disposed at a distal end.

In some embodiments of the device, each magnetic sensor array includes one or more magnetic sensors having an analyte-specific probe bound to a surface of the magnetic sensor.

In some embodiments of the device, each distal end of the elongated regions is sized to fit within separate fluid reservoirs.

In some embodiments of the device, at least one of the magnetic sensor arrays includes two or more distinct magnetic sensors each configured to specifically detect the same analyte.

In some embodiments of the device, at least one of the magnetic sensor arrays includes two or more distinct magnetic sensors each configured to specifically detect a different analyte.

In some embodiments of the device, at least two of the magnetic sensor arrays are configured to specifically detect a different set of analytes.

In some embodiments of the device, the magnetic sensor array includes one or more spin valve sensors.

In some embodiments of the device, the magnetic sensor array includes one or more magnetic tunnel junction sensors.

Embodiments of the present disclosure include a reservoir plate that includes an addressable array of fluid reservoirs having two or more rows of fluid reservoirs and two or more columns of fluid reservoirs, where the fluid reservoirs in each row have the same volume and at least two fluid reservoirs in separate columns have different volumes.

In some embodiments of the reservoir plate, the array of fluid reservoirs includes 24 or more fluid reservoirs.

In some embodiments of the reservoir plate, each fluid reservoir has a volume of 1 mL or less.

In some embodiments, the reservoir plate is configured to operatively couple to a reservoir plate actuator configured to move the reservoir plate along an axis of movement.

In some embodiments, the reservoir plate includes an alignment guide configured to align a longitudinal axis of the reservoir plate parallel to the axis of movement.

Embodiments of the present disclosure include a method for determining whether an analyte is present in a sample. The method includes contacting a magnetic sensor device with a set of samples contained in a set of fluid reservoirs to generate a signal, and determining whether the analyte is present in each sample based on the signal. The magnetic sensor device includes a support with two or more elongated regions each having a magnetic sensor array disposed at a distal end.

In some embodiments of the method, each magnetic sensor array includes one or more magnetic sensors having an analyte-specific probe bound to a surface of the magnetic sensor.

In some embodiments of the method, the contacting includes positioning the magnetic sensor arrays in the set of fluid reservoirs containing the samples.

In some embodiments, the method includes magnetically labeling the samples prior to the contacting.

In some embodiments of the method, the determining includes obtaining a real-time analyte-specific signal from the magnetic sensor arrays as the magnetically-labeled sample contacts the magnetic sensor arrays.

In some embodiments, the method includes contacting the magnetic sensor arrays with a magnetic label after positioning the magnetic sensor arrays in the set of fluid reservoirs containing the sample.

In some embodiments of the method, the contacting the magnetic sensor arrays with the magnetic label includes positioning the magnetic sensor arrays in a second set of fluid reservoirs containing the magnetic label.

In some embodiments of the method, unbound magnetically labeled analytes are not removed from the magnetic sensor arrays.

Embodiments of the present disclosure include a kit that includes a magnetic sensor device and a magnetic label. The magnetic sensor device includes a support with two or more elongated regions each having a magnetic sensor array disposed at a distal end.

In some embodiments of the kit, the magnetic label is a magnetic nanoparticle.

In some embodiments, the kit includes a reservoir plate having a plurality of fluid reservoirs.

DETAILED DESCRIPTION

Figure 1:
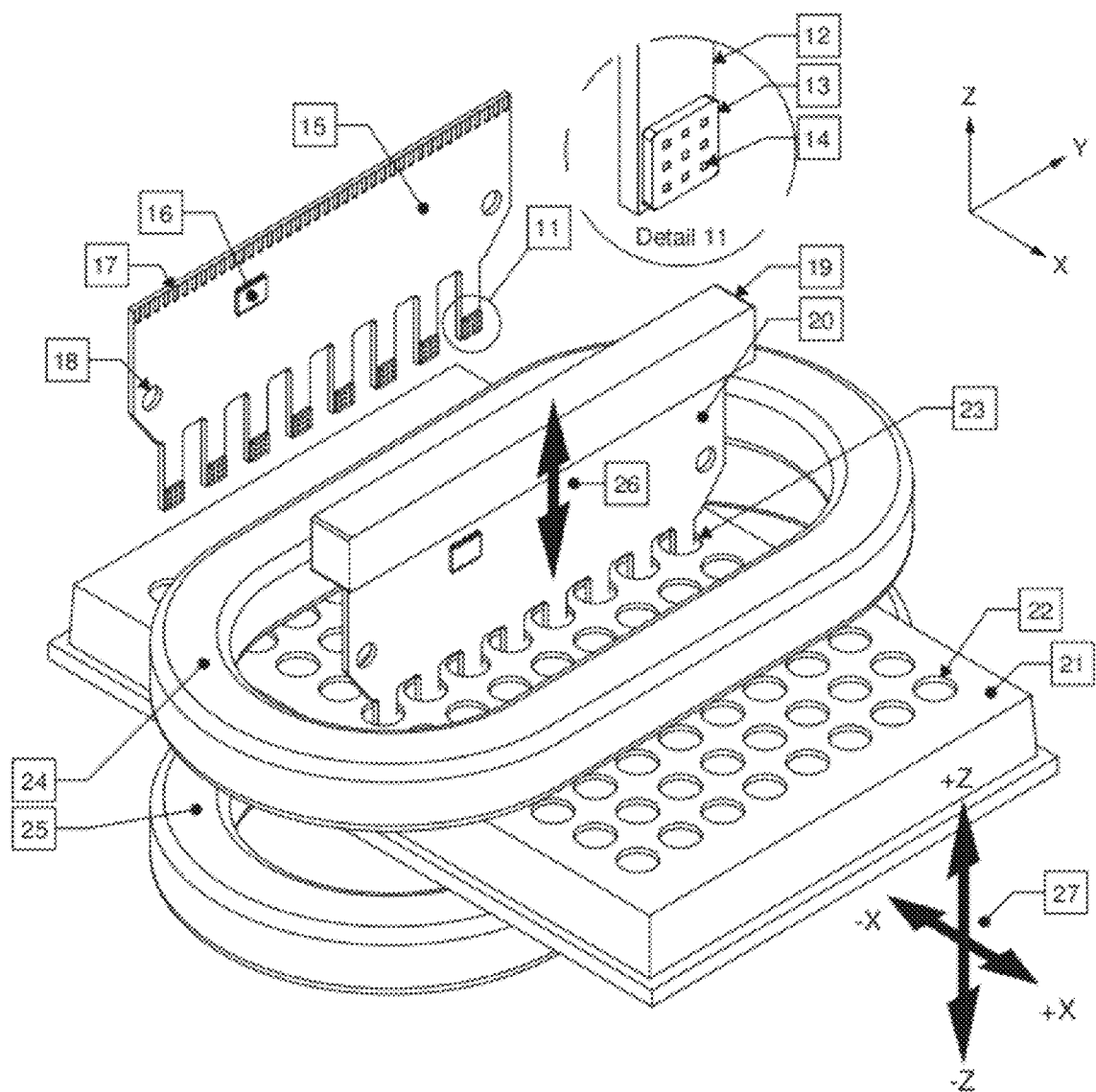
FIG. 1 shows a schematic drawing of a high-throughput system according to embodiments of the present disclosure.

Provided are high-throughput detection systems. The systems include a magnetic sensor device, a magnetic field source and a reservoir plate that includes a plurality of fluid reservoirs. The magnetic sensor device includes a support with two or more elongated regions and a magnetic sensor array disposed at a distal end of each elongated region. Also provided are methods in which the subject high-throughput detection systems find use.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the subject high-throughput detection systems are described first in greater detail, followed by a review of the magnetic sensor devices and reservoir plates that find use in the subject high-throughput detection systems, as well as a discussion of various representative methods in which the subject high-throughput detection systems find use.

High-Throughput Detection Systems

Aspects of the present disclosure include high-throughput detection systems. By "high-throughput," "high-throughput detection," or "high-throughput assay" is meant a plurality of reactions (e.g., assays) are performed in parallel. In some embodiments, a high-throughput method involves performing a plurality of reactions (e.g., assays) substantially simultaneously in parallel. In certain embodiments, the systems include a magnetic sensor device, a magnetic field source, and a reservoir plate (where each of these components is described in greater detail below). The magnetic sensor device includes a support having two or more elongated regions and a magnetic sensor array positioned at a distal end of each elongated region. The reservoir plate includes a plurality of fluid reservoirs. The high-throughput detection systems are configured to position the magnetic sensor arrays in sequential sets of the fluid reservoirs.

By positioning the magnetic sensor arrays in sequential sets of fluid reservoirs, multiple assays can be performed in parallel substantially simultaneously, and therefore providing for a high-throughput format where desired. For example, each fluid reservoir in a first set of fluid reservoirs may individually contain the same or different samples. The system may be configured to position the magnetic sensor arrays in the first set of fluid reservoirs, such as by positioning the distal ends of the elongated regions of the magnetic sensor device, which carry the magnetic sensor arrays, in the first set of fluid reservoirs. The system may be configured to obtain signals from each magnetic sensor array indicating whether one or more analytes is present in each sample. Subsequently, the system may be configured to position the magnetic sensor arrays in a second set of fluid reservoirs, which may individually contain the same or different samples. The system may be configured to position the magnetic sensor arrays in a third, a fourth, a fifth, etc. set of fluid reservoirs, as desired.

To position the magnetic sensor arrays in the fluid reservoirs, the system may have one or more configurations. In certain embodiments, the magnetic sensor device and the reservoir plate are moved relative to each other, e.g., where one component may be stationary and the other component is moved relative to it, or both components are moved relative to each other. For example, the system may be configured to position the magnetic sensor arrays in the fluid reservoirs by moving the magnetic sensor device with respect to the reservoir plate. In other embodiments, the system is configured to position the magnetic sensor arrays in the fluid reservoirs by moving the reservoir plate with respect to the magnetic sensor device. In yet other embodiments, the system is configured to move both the magnetic sensor device and the reservoir plate such that the magnetic sensor device and the reservoir plate are brought into an operative relationship with each other.

In some instances, the reservoir plate is substantially horizontal, such that the plurality of fluid reservoirs is arranged on the top surface of the reservoir plate. The magnetic sensor device may be arranged substantially vertically, such that the elongated regions of the magnetic sensor device are positioned vertically above the fluid reservoirs of the reservoir plate. In order to achieve the desired movements of the magnetic sensor device and the reservoir plate with respect to each other, the system may include one or more actuators. By actuator is meant a device configured to move a part of a mechanism or system. Typically, actuators are operated by a source of energy, usually in the form of an electric current, hydraulic fluid pressure or pneumatic pressure, and convert that energy into a form of motion. Examples of actuators include, but are not limited to, a motor, a pneumatic actuator, a hydraulic piston, a piezoelectric actuator, a transducer, and the like.

In some embodiments, the system may include a first reservoir plate actuator configured to move the reservoir plate into an operative relationship with the magnetic sensor device. For example, the first reservoir plate actuator may be configured to move the reservoir plate such that the distal ends of the elongated regions of the magnetic sensor device are each positioned in separate fluid reservoirs. In some instances, the first reservoir plate actuator is configured to move the reservoir plate along a vertical axis, such that the reservoir plate may be raised and lowered with respect to the magnetic sensor device.

In some embodiments, the system may include a magnetic sensor device actuator configured to move the magnetic sensor device into an operative relationship with the reservoir plate. For example, the magnetic sensor device actuator may be configured to move the magnetic sensor device such that the distal ends of the elongated regions of the magnetic sensor device are each positioned in separate fluid reservoirs. In some instances, the magnetic sensor device actuator is configured to move the magnetic sensor device along a vertical axis, such that the magnetic sensor device may be raised and lowered with respect to the reservoir plate. In certain instances, the magnetic sensor device actuator is configured to move the magnetic sensor device into an operative relationship with the magnetic source. For example, the magnetic sensor device actuator may be configured to position the magnetic sensor arrays of the magnetic sensor device into a region of the magnetic field generated by the magnetic source where an optimal signal can be detected. In some cases, the magnetic sensor device actuator is configured to position the magnetic sensor arrays of the magnetic sensor device into a region of the magnetic field generated of the magnetic sensor device where the direction of the magnetic field is substantially vertical.

In certain embodiments, the system includes one or more additional actuators. For example, the system may include a second reservoir plate actuator. The second reservoir plate actuator may be configured to move the reservoir plate along at least one axis coplanar with the reservoir plate. As described above, the reservoir plate may be positioned substantially horizontally. In these embodiments, the second reservoir plate actuator may be configured to move the reservoir plate in at least one horizontal axis coplanar with the reservoir plate. For instance, the reservoir plate may be in an initial position where the magnetic sensor arrays are aligned with a first set of fluid reservoirs on the reservoir plate. The second reservoir plate actuator may be configured to move the reservoir plate horizontally such that the first set of fluid reservoirs are moved to a position out of alignment with the magnetic sensor arrays and a second set of fluid reservoirs are moved into a position aligned with the magnetic sensor arrays. In these embodiments, the system is configured to position the magnetic sensor arrays in sequential sets of the fluid reservoirs.

In certain embodiments, the system includes a magnetic field source. The magnetic field source may be configured to apply a magnetic field to the magnetic sensor device (e.g., the magnetic sensor arrays) sufficient to produce a DC and/or AC field in the assay sensing area (e.g. in the area where the magnetic sensor arrays are positioned during signal acquisition). In some instances, the magnetic field source is configured to produce a magnetic field with a magnetic field strength of 1 Oe or more, or 5 Oe or more, or 10 Oe or more, or 20 Oe or more, or 30 Oe or more, or 40 Oe or more, or 50 Oe or more, or 60 Oe or more, or 70 Oe or more, or 80 Oe or more, or 90 Oe or more, or 100 Oe or more.

The magnetic field source may be positioned such that a magnetic field is produced in the area where the magnetic sensor arrays are positioned when the magnetic sensor device is in use. In some cases, the magnetic field source is configured to generate a uniform, controllable magnetic field around the set of fluid reservoirs on the reservoir plate where an assay is being performed. The magnetic field source may include one or more, such as two or more, three or more, four or more magnetic field generating components. In certain embodiments, the system includes two magnetic field sources positioned on opposite sides of the reservoir plate. In some cases, the magnetic field source may include one or more electromagnets, such as coil electromagnets. The coil electromagnets may include wire-wound coils. For example, the magnetic field source may include two electromagnets arranged above and below the reservoir plate in a Helmholtz coil geometry.

Embodiments of the systems further include computer-based systems. The systems may be configured to qualitatively and/or quantitatively assess binding interactions as described above. A "computer-based system" refers to the hardware, software, and data storage components used to analyze the signals from the magnetic sensors. The hardware of the computer-based systems may include a central processing unit (CPU), inputs, outputs, and data storage components. Any of a variety of computer-based systems is suitable for use in the subject systems. The data storage components may include any computer readable medium that includes a device for recording signals from the magnetic sensor arrays, or an accessible memory component that can store signals from the magnetic sensor arrays.

To "record" data, programming or other information on a computer readable medium refers to a process for storing information, using any such methods as known in the art. Any convenient data storage structure may be chosen, depending on the method used to access the stored information. A variety of data processor programs and formats can be used for storage, e.g. word processing text file, database format, etc.

In certain embodiments, the system includes an activation and signal processing unit. The activation and signal processing unit may be configured to operably couple to the magnetic sensor device. In some instances, the activation and signal processing unit is electrically coupled to the magnetic sensor device. The activation and signal processing unit may be electrically coupled such as to provide bi-directional communication to and from the magnetic sensor device. For example, the activation and signal processing unit may be configured to provide power, activation signals, etc. to components of the magnetic sensor device, such as, but not limited to the magnetic sensor arrays. As such, the activation and signal processing unit may include an activation signal generator. The activation signal generator may be configured to provide power, activation signals, etc. to components of the analyte detection device, such as, but not limited to the magnetic sensor arrays. In some instances, the activation and signal processing unit is configured to apply a voltage across the magnetic sensor arrays ranging from 1 mV to 100 V, such as 100 mV to 50 V, including 500 mV to 10 V, for example, 500 mV to 5 V. In some cases, the activation and signal processing unit is configured to apply a voltage across the magnetic sensor arrays of 1 V.

Additionally, the activation and signal processing unit may be configured to receive signals from the magnetic sensor device, such as from the magnetic sensor arrays of the magnetic sensor device. The signals from the magnetic sensor arrays of the magnetic sensor device may be used to detect the presence of one or more analytes in the samples. In some instances, the activation and signal processing unit may include a processor configured to output an analyte detection result in response to receiving signals from the magnetic sensor arrays. Thus, the processor of the activation and signal processing unit may be configured to receive signals from the magnetic sensor device, process the signals according to a predetermined algorithm, obtain a result related to the presence of one or more analytes in the samples, and output the result to a user in a human-readable or an audible format.

A "processor" references any hardware and/or software combination that will perform the functions required of it. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid-state device based). For example, a magnetic medium, optical disk or solid-state memory device may carry the programming, and can be read by a suitable reader communicating with the processor.

In some instances, the subject systems are configured to modulate the current applied to the magnetic sensor arrays (e.g., the sense current). The subject systems may also be configured to modulate the magnetic field generated by the magnetic field source. Modulating the sense current and the magnetic field may facilitate a minimization in signal noise, and thus a maximization in the signal to noise ratio. Additional aspects of modulating the sense current and the magnetic field are described in more detail in U.S. application Ser. No. 12/759,584, entitled "Methods and Devices for Detecting the Presence of an Analyte in a Sample, filed on Apr. 13, 2010, the disclosure of which is incorporated herein by reference in its entirety.

Embodiments of the subject systems may also include the following components: (a) a wired or wireless communications module configured to transfer information between the system and one or more users, e.g., via a user computer, as described below; and (b) a processor for performing one or more tasks involved in the qualitative and/or quantitative analysis of the signals from the magnetic sensors. In certain embodiments, a computer program product is provided that includes a computer-usable medium having control logic (e.g., a computer software program, including program code)

stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the magnetic sensor device and activation and signal processing unit, the systems may include a number of additional components, such as, but not limited to: data output devices, e.g., monitors, speakers, etc.; data input devices, e.g., interface ports, buttons, switches, keyboards, etc.; fluid handling components, e.g., microfluidic components; power sources; power amplifiers; wired or wireless communication components; etc. For example, the systems may include fluid handling components, such as microfluidic fluid handling components. In certain embodiments, the microfluidic fluid handling components are configured to deliver a fluid to the fluid reservoirs of the reservoir plate. In some cases, the fluid includes one or more of the following: an assay composition, a sample, a magnetic label, a capture probe, a reagent, and the like. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less.

In certain embodiments, the system is a high-sensitivity analyte detector. By "high-sensitivity" is meant that the system is configured to detect an analyte in a sample, where the concentration of the analyte in the sample is low. In some cases, the system is configured to produce a detectable signal indicating the presence of an analyte of interest in a sample where the concentration of the analyte in the sample is 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less.

In certain embodiments, the systems include a display. The display may be configured to provide a visual indication of an analyte detection result obtained from the activation and signal processing unit, as described above. The display may be configured to display a qualitative analyte detection result. For instance, the qualitative display may be configured to display qualitative indicators to a user that a sample includes or does not include a specific analyte of interest. In some embodiments, the display may be configured to display an analyte detection result, where the analyte detection result is a quantitative result, e.g., a quantitative measurement of the concentration of an analyte in a sample. For example, in embodiments where the system is configured to output a quantitative analyte detection result, the system may include a display configured to display the quantitative analyte detection result.

An example of a system according to embodiments of the present disclosure is shown in FIG. 1. Magnetic sensor arrays (13) located at the distal ends of the elongated regions (11) of a vertically positioned magnetic sensor device (15). The magnetic sensor device (15) is an electronic printed circuit board (12) which carries the signals from the magnetic sensor array (13) to the activation and signal processing unit. The magnetic sensor array (13) has exposed at its surface one or more magnetic sensors (14).

The magnetic sensor device (15) includes 8 elongated regions, each with a magnetic sensor array (13), which makes it possible to manipulate multiple magnetic sensor arrays simultaneously, while also providing for a larger and more reliable set of electrical contacts (17) than an individual magnetic sensor array would have. Optional alignment guides (18) are configured to align the magnetic sensor device (15) in the system. The magnetic sensor device (15) optionally includes a programmable memory (16), which prior to and during the use of the magnetic sensor device can be programmed with relevant information such as: calibration data for each individual sensor; a record of how the biochip has been prepared with surface functionalization molecules prior to the assay; a record of all completed assay steps; a record about which sample was measured; a record of the measurement results; and the like.

To perform a measurement with the magnetic sensor device, the magnetic sensor device is first inserted into an electrical signal socket (19) which receives the signals from the magnetic sensor arrays for further processing. The signal socket (19) and its connected magnetic sensor device (20) are then lowered so that the elongated regions of the magnetic sensor device are positioned in the sample-containing fluid reservoirs (23) on a reservoir plate (21). Additional fluid reservoirs (22) on the reservoir plate may hold additional reagents to which the sensors are exposed during the assay protocol.

In certain embodiments, the magnetic sensors (14) are magnetoresistive sensors, such as spin-valve or magnetic-tunnel-junction sensors, which can detect superparamagnetic or antiferromagnetic magnetic labels with a diameter ranging from nanometer scale to micrometer scale that are used to label analytes of interest in the sample. In certain embodiments, two magnetic field sources (24) and (25) (e.g., magnetic field generating wire-wound coils) are arranged above and below the reservoir plate (21) in a Helmholtz coil geometry to generate a uniform and electrically controllable magnetic field around the fluid reservoirs (23) on the reservoir plate (21).

In certain embodiments, the signal socket (19) and its attached magnetic sensor device (20) can be raised and lowered along the z-axis as indicated by the arrow (26). In other embodiments, the reservoir plate (21) may be operatively coupled to a reservoir plate actuator, which is configured to move the reservoir plate along the z-axis towards and away from the magnetic sensor device. The reservoir plate (21) can be moved along at least one axis in the plane, such as in either direction along the x-axis or in either direction along the z-axis, as indicated by the arrow (27). This makes it possible to move the magnetic sensor device (20) from one row of fluid reservoirs on the reservoir plate (21) to the next row of fluid reservoirs.

Magnetic Sensor Devices

Aspects of the present disclosure also include a magnetic sensor device for use in the systems described above. The magnetic sensor device includes a support that has two or more elongated regions. In some embodiments, each elongated region includes a magnetic sensor array disposed at a distal end.

In certain embodiments, the support of the magnetic sensor device includes a central body region and two or more elongated regions. The two or more elongated regions may extend from the body of the support along one edge of the support. For example the proximal ends of the elongated regions may be connected to or be formed from the same piece of material as the support, with the distal ends of the elongated regions extending away from the body of the support. The two or more elongated regions may be arranged substantially parallel to each other and may each have approximately the same dimensions, such that the two or more elongated regions are arranged to form a comb-like structure extending from the body of the support along one edge of the support.

The elongated regions may be configured to fit within separate fluid reservoirs of the reservoir plate. For example, each distal end of the elongated regions may be sized to fit within separate fluid reservoirs. As such, the elongated regions may have dimensions (e.g., width and thickness) less than the interior dimensions of the fluid reservoirs of the reservoir plate. For instance, if the fluid reservoirs of the reservoir plate are round, then the width and thickness of the elongated regions may be less than the diameter of the fluid reservoirs. In embodiments where the fluid reservoirs are rectangular in shape, then the width and thickness of the elongated regions may be less than the dimensions of the corresponding width and thickness of the fluid reservoirs. In certain embodiments, the elongated regions have a thickness of 10 mm or less, such as 9 mm or less, including 8 mm or less, or 7 mm or less, or 6 mm or less, or 5 mm or less, or 4 mm or less, or 3 mm or less, or 2 mm or less, or 1 mm or less. In certain embodiments, the elongated regions have a width of 25 mm or less, such as 20 mm or less, including 15 mm or less, or 10 mm or less, or 5 mm or less. In some instances, the elongated regions have a length sufficient to position the distal ends of the elongated regions in the fluid reservoirs while still having a portion of the proximal end of the elongated regions extending above the top surface of the reservoir plate, such that the support body of the magnetic sensor device does not contact the reservoir plate. For example, the elongated regions may have a length that is greater than the depth of the fluid reservoirs. In certain embodiments, the elongated regions have a length of 5 mm or more, such as 10 mm or more, including 15 mm or more, or 20 mm or more or 25 mm or more or 30 mm or more.

In certain embodiments, the support of the magnetic sensor device is shaped as a rectangular solid (although other shapes are possible), having a length ranging from 1 cm to 20 cm, such as 1 cm to 10 cm, including 1 cm to 5 cm; a width ranging from 1 cm to 20 cm, such as 1 cm to 10 cm, including 1 cm to 5 cm, or 1 cm to 3 cm; and a thickness ranging from 1 mm to 10 mm, such as 1 mm to 5 mm, including 1 mm to 3 mm.

In certain embodiments, each elongated region includes a magnetic sensor array disposed at a distal end of the elongated regions. For example, the magnetic sensor device may include a magnetic sensor array disposed at a distal end of each elongated region. In some instances, the magnetic sensor device may include one or more elongated regions that do not include a magnetic sensor array. For instance, one or more elongated regions may be configured as a control or reference sensor.

In certain embodiments, the magnetic sensor arrays are positioned on the distal end of the elongated regions such that when the distal ends of the elongated regions are positioned in the fluid reservoirs of the reservoir plate, the magnetic sensor arrays are positioned in the fluid reservoirs. Each magnetic sensor array may be positioned such that substantially the entire array is in its corresponding fluid reservoir. For example, the magnetic sensor arrays may be positioned on the distal end of the elongated regions adjacent to the edge of the distal end of the elongated region, such as substantially at the edge of the distal end of the elongated region, or within a certain distance from the edge of the distal end of the elongated region, e.g., 5 mm or less, or 4 or less, or 3 mm or less, or 2 mm or less, or 1 mm or less.

Magnetic Sensor Arrays

The magnetic sensor arrays may have a variety of different configurations, e.g., with respect to magnetic sensor configuration. In certain embodiments, the subject magnetic sensor arrays are arranged on a biochip (e.g., a biosensor chip). By "biochip" or "biosensor chip" is meant a magnetic sensor array that includes a support surface which displays two or more distinct magnetic sensors on the support surface. In certain embodiments, the magnetic sensor device includes a support surface with an array of magnetic sensors.

An "array" includes any two-dimensional or substantially two-dimensional (as well as a three-dimensional) arrangement of addressable regions, e.g., spatially addressable regions. An array is "addressable" when it has multiple sensors positioned at particular predetermined locations (e.g., "addresses") on the array. Array features (e.g., sensors) may be separated by intervening spaces. Any given support may carry one, two, four or more arrays disposed on a front surface of the support. Depending upon the use, any or all of the arrays may be the same or different from one another and each may contain multiple distinct magnetic sensors. An array may contain one or more, including 2 or more, 4 or more, 8 or more, 10 or more, 50 or more, 100 or more, 250 or more, 500 or more, 750 or more, 1000 or more magnetic sensors. For example, 64 magnetic sensors can be arranged into an 8×8 array. In certain embodiments, the magnetic sensors can be arranged into an array with an area of less than 10 cm$^2$, or less than 5 cm$^2$, e.g., less than 1 cm$^2$, including less than 50 mm$^2$, less than 20 mm$^2$, such as less than 10 mm$^2$, or even smaller. For example, magnetic sensors may have dimensions in the range of 10 μm×10 μm to 200 μm×200 μm, including dimensions of 100 μm×100 μm or less, such as 75 μm×75 μm or less, for instance 50 μm×50 μm or less.

In certain embodiments, at least some, or all, of the magnetic sensors have an analyte-specific probe (e.g., a surface capture ligand) stably associated with a surface of the sensor. For example, each magnetic sensor array may include one or more magnetic sensors having an analyte-specific probe bound to a surface of the magnetic sensor. Where a given array includes two or more magnetic sensors, each sensor may have the same or different analyte-specific probe associated with its surface. For example, a magnetic sensor array may include two or more distinct magnetic sensors each configured to specifically detect the same analyte. In some cases, different analyte-specific probes may be present on the sensor surfaces of such devices, such that each different analyte-specific probe specifically binds to a distinct analyte. For instance, a magnetic sensor array may include two or more distinct magnetic sensors each configured to specifically detect a different analyte. In other cases, the magnetic sensor devices include magnetic sensors that are free of any analyte-specific probes, such that the surface of the magnetic sensor is functionalized to bind directly to the analyte. In some instances, the magnetic sensor includes a blocking layer disposed over the surface of the magnetic sensor. The blocking layer may be configured to inhibit the binding of any analyte-specific probes or analyte to the surface of the magnetic sensor (e.g., where such blocked magnetic sensors may serve as sources of reference or control electrical signals).

As described above, in certain embodiments, the magnetic sensor device includes two or more elongated regions with a magnetic sensor array disposed on each elongated region. As such, the magnetic sensor device includes two or more magnetic sensor arrays. As described above, each magnetic sensor array may have one or more magnetic sensors with each magnetic sensor configured to detect the same or different analytes. Thus, each magnetic sensor array on the magnetic sensor device may be configured to detect the same set or different sets of analytes. For example, a magnetic sensor device may include two or more distinct magnetic sensor arrays each configured to specifically detect the same set of analytes. In other cases, a magnetic sensor device may include two or more distinct magnetic sensors each configured to specifically detect a different set of analytes.

In certain embodiments, areas in between the magnetic sensors in an array may be present which do not carry any analyte-specific probes or are not functionalized to bind directly to the analyte. Such inter-sensor areas, when present, may be of various sizes and configurations. In some instances, these inter-sensor areas may be configured to inhibit or prevent fluid movement among different sensors, e.g., where the inter-sensor areas are coated with hydrophobic materials and/or fluid barriers, such as walls.

Electronic communication elements, e.g., conductive leads, may be present which are configured to electronically couple the magnetic sensors to components of the system, such as processors, displays, etc. Additionally, a given magnetic sensor device may include a variety of other components in addition to the magnetic sensor array. Additional magnetic sensor device components may include, but are not limited to: signal processing components, power sources, fluid handling components, wired or wireless communication components, etc.

In certain embodiments, the magnetic sensor device is configured to produce a detectable signal from a minimum amount of sample. In some instances, the magnetic sensor device is configured to produce a detectable signal from a sample size of 10 mL or less, or 5 mL or less, or 3 mL or less, or 1 mL or less, such as 500 µL or less, including 100 µL or less, for example 50 µL or less, or 25 µL or less, or 10 µL or less. As such, in some cases, the fluid reservoirs of the reservoir plate may be configured to receive a minimum amount of sample needed to produce a detectable signal. For example, the fluid reservoirs may be configured to receive a sample of 10 mL or less, or 5 mL or less, or 3 mL or less, or 1 mL or less, such as 500 µL or less, including 100 µL or less, for example 50 µL or less, or 25 µL or less, or 10 µL or less.

In some embodiments, the magnetic sensor device is configured to connect to a system for detecting the presence of an analyte in a sample. Accordingly, in certain embodiments, the magnetic sensor device does not include a magnetic field source. The magnetic field source may be included in the system for detecting the presence of an analyte in the sample and, thus not included in the magnetic sensor device. Thus, the assay protocol may include operably coupling the magnetic sensor device to the system for detecting the presence of an analyte in the sample. In some instances, the magnetic sensor device may be operably coupled to an activation and signal processing unit of the system, as described above. The magnetic sensor device may include one or more electrical contacts configured to electrically connect the magnetic sensor device to the system, such as to the activation and signal processing unit of the system. The electrical contacts may be arranged along an edge of the magnetic sensor device, such as along an edge of the magnetic sensor device opposite from the edge of the magnetic sensor device where the elongated regions are positioned.

In certain embodiments, the magnetic sensor device includes a programmable memory. In some cases, the programmable memory is configured to store information, such as information including, but not limited to: calibration data (e.g., calibration data for each magnetic sensor and/or each magnetic sensor array); a record of how the magnetic sensors have been prepared with surface functionalization molecules prior to the assay; a record of completed assay steps; a record about which sample was measured; a record of the measurement results; and the like. In some instances, a barcode may be used instead of, or in addition to, the programmable memory. In embodiments of the magnetic sensor device that include a barcode, information associated with the magnetic sensor device may be stored and retrieved from an information system separate from the magnetic sensor device, such as the activation and signal processing unit of the system.

Magnetic Sensors

As described above, each magnetic sensor array may include one or more magnetic sensors. In some cases, magnetic sensors are sensors configured to detect the presence of nearby magnetic labels without any direct physical contact between the magnetic sensor and the magnetic label. In certain embodiments, the magnetic sensors are configured to detect the presence of an analyte in a sample. For example, a magnetic label may be bound, either directly or indirectly, to an analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

In some instances, the magnetic sensors have a detection range from 1 nm to 200 nm from the surface of the magnetic sensor, such as from 5 nm to 150 nm, including from 5 nm to 100 nm, such as from 5 nm to 50 nm, including from 5 nm to 25 nm from the surface of the magnetic sensor. By "detection range" is meant the distance from the surface of the magnetic sensor where the presence of a magnetic label will induce a detectable signal in the magnetic sensor. In some cases, magnetic labels positioned close enough to the surface of the magnetic sensor to be within the detection range of the magnetic sensor will induce a detectable signal in the magnetic sensor. In certain instances, magnetic labels positioned at a distance from the surface of the magnetic sensor that is greater than the detection range of the magnetic sensor will not induce a detectable or non-negligible signal in the magnetic sensor. For example, a magnetic label may have a magnetic flux that is proportional to $1/r^3$, where r is the distance between the magnetic sensor and the magnetic label. Thus, only those magnetic labels that are positioned in close proximity (e.g., within the detection range of the magnetic sensor) will induce a detectable signal in the magnetic sensor.

In certain embodiments, the surface of the magnetic sensor is functionalized to bind directly to an analyte. For example, the surface of the magnetic sensor may be functionalized to provide for covalent binding or non-covalent association of the analyte and magnetic sensor, including, but not limited to, non-specific adsorption, binding based on electrostatic interactions (e.g., ion-ion pair interactions), hydrophobic interactions, hydrogen bonding interactions, and the like.

In some instances, the surface of the magnetic sensor includes an analyte-specific probe (e.g., a surface capture ligand) that specifically binds to an analyte. The analyte-specific probe may be bound to the surface of the magnetic sensor. For instance, a cationic polymer such as polyethyleneimine (PEI) can be used to nonspecifically bind charged antibodies to the sensor surface via physiabsorption. Alternatively, a covalent chemistry can be used utilizing free amines or free thiol groups on the analyte-specific probe to covalently bind the analyte-specific probe to the surface of the magnetic sensor. For example, an N-hydroxysuccinimide (NHS) to 1-ethyl-3-(3-dimethylaminopropyl) carbodiimide (EDC) coupling system may be used to covalently bind the analyte-specific probe to the surface of the magnetic sensor.

The analyte-specific probe may include one member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like. In certain embodiments, the surface of the magnetic sensor includes an antibody that specifically binds to an analyte of interest. Accordingly, contacting the magnetic sensor with an assay composition that includes the analyte of interest may result in binding of the analyte to the analyte-specific probe (e.g., antibody) bound to the surface of the magnetic sensor.

Magnetic sensors that may be used in the subject methods may vary, and include any type of sensor that provides a detectable signal when a magnetic label is positioned near the surface of the magnetic sensor. For example, magnetic sensors may include, but are not limited to, giant magnetoresistive (GMR) sensors, such as spin valve detectors, magnetic tunnel junction (MTJ) detectors, and the like.

In certain embodiments, the magnetic sensor is configured to generate an electrical signal in response to a magnetic label in proximity to a surface of the magnetic sensor. Magnetic sensors may include, but are not limited to, magnetoresistive sensor devices, including giant magnetoresistive (GMR) sensors. For example, the magnetic sensors may be configured to detect changes in the resistance of the magnetic sensor induced by changes in the local magnetic field. In some cases, binding of a magnetic label (e.g., a magnetic nanoparticle label) in close proximity to the magnetic sensor, as described above, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. In certain embodiments, the magnetic sensors are configured to detect changes in resistance of 1 Ohm or less, such as 500 mOhm or less, including 100 mOhm or less, or 50 mOhm or less, or 25 mOhm or less, or 10 mOhm or less, or 5 mOhm or less, or 1 mOhm or less.

In certain cases, GMR sensors are multilayer thin film structures. GMR sensors may include alternating layers of a ferromagnetic material and a non-magnetic material. The ferromagnetic material may include, but is not limited to, Permalloy (NiFe), iron cobalt (FeCo), nickel iron cobalt (NiFeCo), nickel oxide (NiO), cobalt oxide (CoO), nickel cobalt oxide (NiCoO), ferric oxide ($Fe_2O_3$), and the like. In some cases, the non-magnetic material is a conductive non-magnetic material, such as, but not limited to copper, gold, silver, etc. In certain embodiments, the ferromagnetic layer has a thickness of 1 nm to 50 nm, such as 5 nm to 25 nm, including 5 nm to 10 nm. In some instances, the non-magnetic layer has a thickness of 1 nm to 50 nm, such as 1 nm to 25 nm, including 1 nm to 10 nm.

In some cases, GMR sensors include, but are not limited to spin valve detectors and magnetic tunnel junction (MTJ) detectors, each of which are discussed in more detail below.

Spin-Valve Detectors

In some instances, the magnetic sensor is a spin valve detector. In certain case, the spin valve detector is a multilayer structure that includes a first ferromagnetic layer, a non-magnetic layer disposed on the first ferromagnetic layer, and a second ferromagnetic layer disposed on the non-magnetic layer. The first ferromagnetic layer may be configured to have its magnetization vector fixed in a certain direction. In some cases, the first ferromagnetic layer is called the "pinned layer". The second ferromagnetic layer may be configured such that its magnetization vector can rotate freely under an applied magnetic field. In some cases, the second ferromagnetic layer is called the "free layer".

In certain instances, the electrical resistance of a spin valve detector depends on the relative orientation of the magnetization vector of the free layer to that of the pinned layer. When the two magnetization vectors are parallel, the resistance is the lowest; when the two magnetization vectors are antiparallel, the resistance is the highest. The relative change of resistance is called the magnetoresistance (MR) ratio. In certain embodiments, spin valve detectors have a MR ratio of 1% to 20%, such as 3% to 15%, including 5% to 12%. In some cases, the MR ratio of a spin valve detector is 10% or more in a small magnetic field, e.g., 100 Oe. Changes in the resistance of the spin valve detector due to the presence of magnetic labels near the surface of the spin valve detector may be detected, as described above.

In certain embodiments, the signal from the spin valve detector due to the magnetic label depends on the distance between the magnetic label and the free layer of the spin valve detector. In some cases, the voltage signal from a magnetic label decreases as the distance from the center of the magnetic label to the mid-plane of the free layer increases. Thus, in certain instances, the free layer in the spin valve detector is positioned at the surface of the spin valve detector. Positioning the free layer at the surface of the spin valve detector may minimize the distance between the free layer and any bound magnetic labels, which may facilitate detection of the magnetic labels.

In certain embodiments, the spin valve detector may include a passivation layer disposed on one or more of the spin valve detector surfaces. In some cases, the passivation layer has a thickness of 60 nm or less, such as 50 nm or less, including 40 nm or less, 30 nm or less, 20 nm or less, 10 nm or less. For instance, the passivation layer may have a thickness of 1 nm to 10 nm, such as from 1 nm to 5 nm, including from 1 nm to 3 nm. In certain embodiments, the passivation layer includes gold, tantalum, $SiO_2$, $Si_3N_4$, combinations thereof, and the like.

Magnetic Tunnel Junction Detectors

In certain embodiments, the magnetic sensor is a magnetic tunnel junction (MTJ) detector. In some cases, the MTJ detector includes a multilayer structure that includes a first ferromagnetic layer, an insulating layer disposed on the first ferromagnetic layer, and a second ferromagnetic layer disposed on the insulating layer. The insulating layer may be a thin insulating tunnel barrier, and may include alumina, MgO, and the like. In some cases, electron tunneling between the first and the second ferromagnetic layers depends on the relative magnetization of the two ferromagnetic layers. For example, in certain embodiments, the tunneling current is high when the magnetization vectors of the first and second ferromagnetic layers are parallel and the tunneling current is low when the magnetization vectors of the first and second ferromagnetic layers antiparallel.

In some instances, MTJ detectors have a MR ratio of 1% to 300%, such as 10% to 250%, including 25% to 200%. Changes in the resistance of the MTJ detector due to the presence of magnetic labels near the surface of the MTJ detector may be detected, as described above.

In certain embodiments, the second ferromagnetic layer (e.g., the layer of the MTJ detector positioned at the surface of the MTJ detector) includes two of more layers. For example, the second ferromagnetic layer may include a first layer and a second layer disposed on the first layer. In some cases, the first layer is a thin metallic layer (e.g., a gold layer). The thin metallic layer may have a thickness of 60 nm or less, such as 50 nm or less, including 40 nm or less, 30 nm or less, 20 nm or less, or 10 nm or less. The second layer may include a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like.

In some cases, the MTJ detector is configured such that the distance between an associated magnetic label and the top surface of the free layer ranges from 1 nm to 200 nm, such as from 5 nm to 150 nm, including from 5 nm to 100 nm, such as from 5 nm to 50 nm, including from 5 nm to 25 nm.

As described above for spin valve detectors, in certain instances, the MTJ detector may include a passivation layer disposed on one or more of the MTJ detector surfaces. In some instances, the passivation layer has a thickness of 60 nm or less, such as 50 nm or less, including 40 nm or less, 30 nm or less, 20 nm or less, 10 nm or less. For example, the passivation layer may have a thickness of 1 nm to 10 nm, such as from 1 nm to 5 nm, including from 1 nm to 3 nm. In some cases, the passivation layer includes gold, tantalum, a tantalum alloy, a tantalum oxide, aluminum, an aluminum alloy, an aluminum oxide, $SiO_2$, $Si_3N_4$, combinations thereof, and the like.

Spin valve detectors (also referred to as spin valve film detectors) and magnetic tunnel junction (MTJ) detectors, are further described in U.S. Ser. No. 12/234,506, filed Sep. 19, 2008, and entitled "Analyte Detection with Magnetic Sensors", the disclosure of which is hereby incorporated by reference in its entirety. Detectors are further described in U.S. patent application Ser. No. 10/829,505, filed Apr. 22, 2004 and entitled "Magnetic nanoparticles, magnetic detector arrays, and methods for their use in detecting biological molecules", the disclosure of which is hereby incorporated by reference in its entirety.

Reservoir Plates

Aspects of the present disclosure also include a reservoir plate. The reservoir plate includes an addressable array of fluid reservoirs. The array of fluid reservoirs includes two or more rows of fluid reservoirs and two or more columns of fluid reservoirs. The fluid reservoirs may be any of a variety of configurations, where the fluid reservoirs are configured to hold a sample in contact with the magnetic sensor arrays. Accordingly, configurations of the fluid reservoirs may include, but are not limited to: cylindrical well configurations, square well configurations, rectangular well configurations, round bottom well configurations, and the like. For instance, the fluid reservoirs may include walls that separate one fluid reservoir from adjacent fluid reservoirs. The walls may be substantially vertical with respect to the surface of the reservoir plate. In some cases, the walls of each fluid reservoir define a volume of space that may receive a volume of sample equal to or less than the volume of space defined by the fluid reservoir.

In certain embodiments, the fluid reservoirs in each row have the same volume. For example, the fluid reservoirs in a row may have substantially the same shape and size, such that the fluid reservoirs in the row have substantially the same volume. In certain embodiments, having a row of fluid reservoirs each having the same volume allows simultaneous positioning of two or more of magnetic sensor arrays into a set (e.g., row) of fluid reservoirs that each have the same volume. In some cases, this arrangement of fluid reservoirs facilitates performing the same assay step on each magnetic sensor array as the magnetic sensor device is positioned in each fluid reservoir in a row of fluid reservoirs.

In some instances, the fluid reservoirs in each row of fluid reservoirs have the same volume, such that all the fluid reservoirs on the reservoir plate have the same volume. In other embodiments, at least two fluid reservoirs in separate columns have different volumes. For example, a first row of fluid reservoirs may have a first volume, and a second row of fluid reservoirs may have a second volume different from the first volume. Thus, two fluid reservoirs in separate columns have different volumes. In these embodiments, having a first row of fluid reservoirs with a different volume than a second row of fluid reservoirs may facilitate performing different assay steps on the magnetic sensor arrays as the magnetic sensor device is positioned sequentially in the first and then second row of fluid reservoirs.

In certain embodiments, the array of fluid reservoirs on the reservoir plate includes 6 or more fluid reservoirs, or 24 or more fluid reservoirs, such as 36 or more, including 48 or more, or 96 or more, or 384 or more, or 1536 or more fluid reservoirs. In some instances, the fluid reservoirs have an individual volume of 10 mL or less, or 5 mL or less, or 3 mL or less, or 1 mL or less, such as 500 μL or less, including 100 μL or less, for example 50 μL or less, or 25 μL or less, or 10 μL or less.

In certain embodiments, the reservoir plate is configured to operatively couple to a reservoir plate actuator configured to move the reservoir plate along an axis of movement. As described above, the system may include a first reservoir plate actuator configured to move the reservoir plate into an operative relationship with the magnetic sensor device (e.g., vertically towards and away from the magnetic sensor device). In certain cases, moving the reservoir plate towards and away from the magnetic sensor device while the magnetic sensor device is kept substantially stationary may facilitate an increase in the signal to noise ratio (e.g., a reduction in the level of noise) for the acquired signal. In some embodiments, the system may include a second reservoir plate actuator configured to move the reservoir plate along at least one axis coplanar with the reservoir plate. As such, the reservoir plate may include an alignment guide configured to align an axis of the reservoir plate parallel to an axis of movement of the reservoir plate. As described above, the reservoir plate may be moved by the first and/or second reservoir plate actuators in any of three dimensions. Thus, the alignment guide may align an axis of the reservoir plate parallel to an axis in one of the three dimensions. For example, the alignment guide may be configured to align the vertical axis of the reservoir plate parallel to a vertical axis of movement (e.g., vertically towards and away from the magnetic sensor device). In some cases, the alignment guide is configured to align a horizontal axis of the reservoir plate parallel to a horizontal axis of movement. For instance, the alignment guide may be configured to align a longitudinal axis of the reservoir plate parallel to an axis normal to the magnetic sensor device. In some instances, the alignment guide may be configured to align a transverse axis of the reservoir plate parallel to an axis parallel to the magnetic sensor device.

Figure 2A:
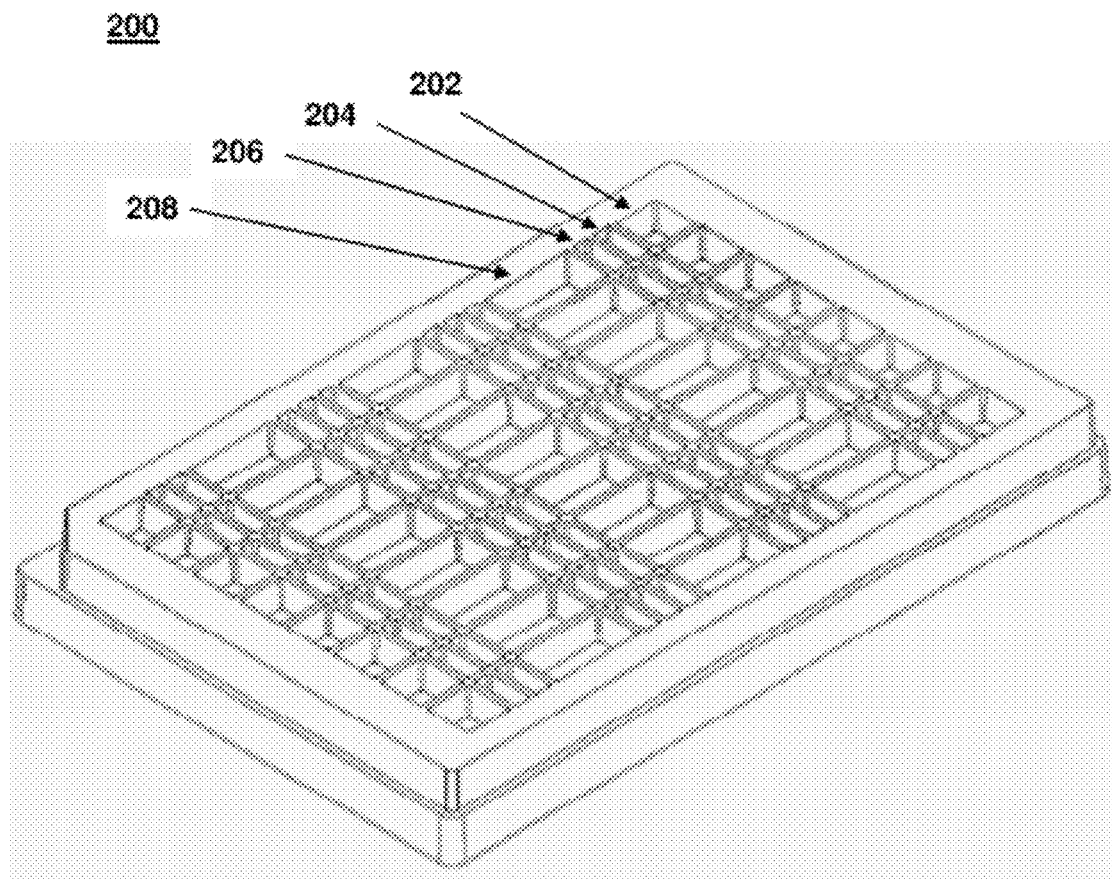
FIG. 2A shows a schematic drawing of a perspective view of a reservoir plate according to embodiments of the present disclosure.
Figure 2B:
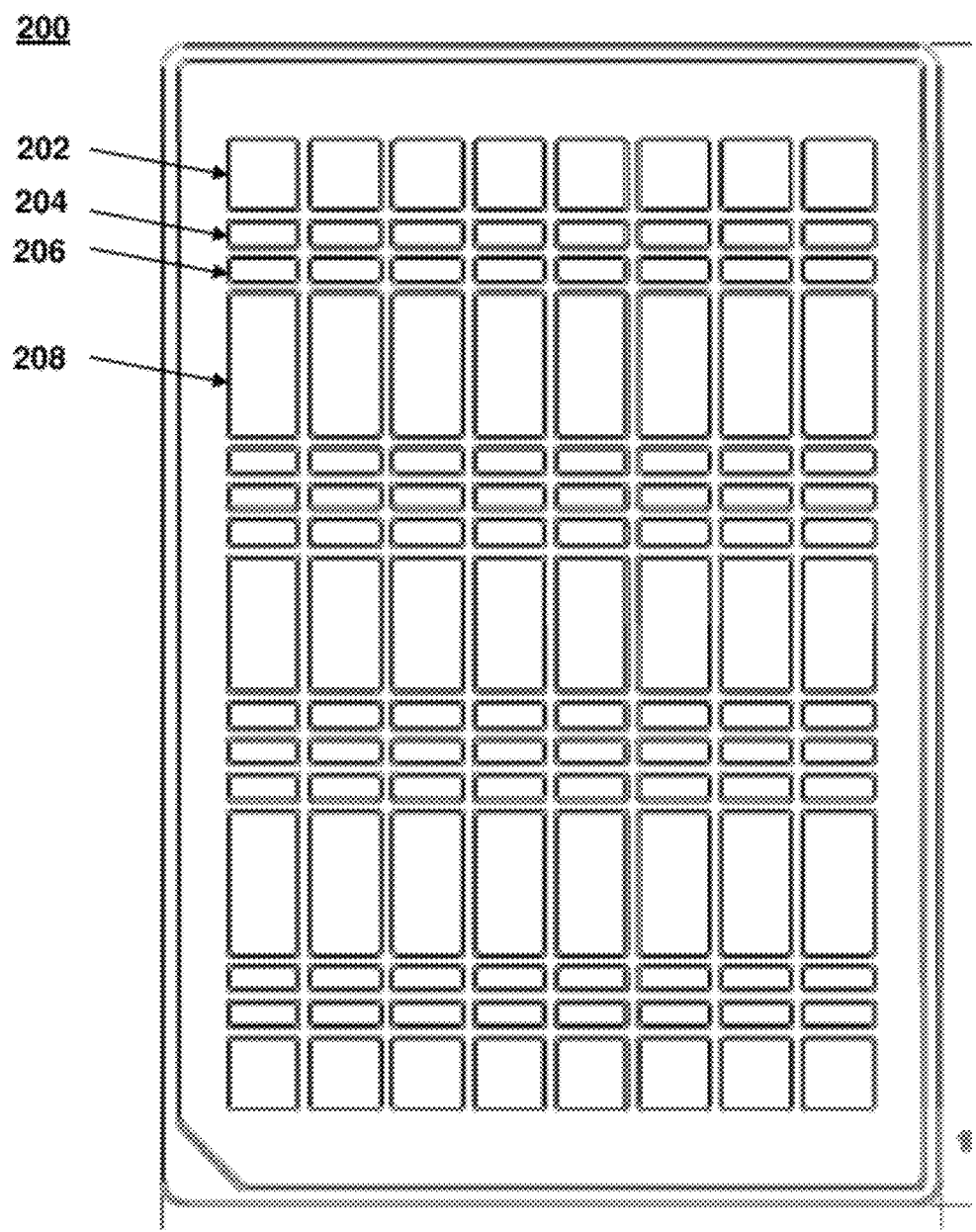
FIG. 2B shows a schematic drawing of a top view of a reservoir plate according to embodiments of the present disclosure.

FIGS. 2A and 2B show schematic drawings of a reservoir plate according to embodiments of the present disclosure. FIG. 2A shows a schematic drawing of a perspective view of a reservoir plate (200) according to embodiments of the present disclosure. As shown in FIG. 2A, a first row of fluid reservoirs (202) is configured to have fluid reservoirs that each have substantially the same volume (e.g., a first volume). A second row of fluid reservoirs (204) is configured to have fluid reservoirs that each has substantially the same volume (e.g., a second volume). As shown in FIG. 2A, the second volume is less than the first volume. A third row of fluid reservoirs (206) is configured to have fluid reservoirs that each has substantially the same volume (e.g., a third volume). As shown in FIG. 2A, the third volume is substantially equivalent to the second volume. A fourth row of fluid reservoirs (208) is configured to have fluid reservoirs that each has substantially the same volume (e.g., a fourth volume). As shown in FIG. 2A, the fourth volume is greater than the first and second volumes. As such, the reservoir plate (200) includes rows of fluid reservoirs, where each fluid reservoir in an individual row of fluid reservoirs may have the same volume. In addition, fluid reservoirs in different rows of fluid reservoirs may have the same or different volumes.

FIG. 2B shows a schematic drawing of a top view of a reservoir plate according to embodiments of the present disclosure.

Methods

Aspects of the present disclosure also include a method for determining whether an analyte is present in a sample. The method includes contacting a magnetic sensor device with a set of samples contained in a set of fluid reservoirs to generate a signal. In addition, the method includes determining whether the analyte is present in each sample based on the signal.

In certain embodiments, the method includes sequentially contacting the magnetic sensor arrays of the magnetic sensor device with sets of assay fluids contained in sets of fluid reservoirs. The method may include contacting the magnetic sensor arrays with a first set of assay fluids in a first set of fluid reservoirs. Then, the method may include contacting the magnetic sensor arrays with a second set of assay fluids in a second set of fluid reservoirs. Subsequently, the method may include contacting the magnetic sensor arrays with a third set of assay fluids in a third set of fluid reservoirs. The magnetic sensor arrays may be contacted with additional sets of assay fluids in additional sets of fluid reservoirs as desired.

To contact the magnetic sensor arrays with sequential sets of assay fluids in sequential sets of fluid reservoirs, the method may include positioning the magnetic sensor arrays in sequential sets of fluid reservoirs. For example, the method may include positioning the reservoir plate such that a first set (e.g., first row) of fluid reservoirs is aligned with the magnetic sensor arrays on the elongated regions of the magnetic sensor device. The method may then include moving the reservoir plate (e.g., in a vertical direction towards the magnetic sensor device) such that the magnetic sensor arrays are positioned in the first set of fluid reservoirs. In some instances, the method includes moving the magnetic sensor device (e.g., in a vertical direction towards the reservoir plate) such that the magnetic sensor arrays are positioned in the first set of fluid reservoirs. After a desired amount of time, the magnetic sensor arrays may be removed from the first set of fluid reservoirs by moving one or both of the reservoir plate and the magnetic sensor device (e.g., in a vertical direction away from each other) such that the magnetic sensor arrays are not positioned in the first set of fluid reservoirs. Next, the method may include positioning the reservoir plate such that a second set (e.g., second row) of fluid reservoirs is aligned with the magnetic sensor arrays on the elongated regions of the magnetic sensor device. For example, the method may include moving the reservoir plate in a horizontal direction such that the second set of fluid reservoirs is aligned with the magnetic sensor arrays. Then, the method may include positioning the magnetic sensor arrays in the second set of fluid reservoirs, using a similar process to that described above.

As described above, each set of fluid reservoirs (e.g., each row of fluid reservoirs) may contain the same or different assay fluids, such that a parallel group of assays may be performed at the same time. For example, a first set of fluid reservoirs may contain a sample to be analyzed for the presence of one or more specific analytes. A second set of fluid reservoirs may contain a capture probe that specifically binds to the analyte of interest. A third set of fluid reservoirs may contain a magnetic label. As such, the assay method may include sequentially contacting the magnetic sensor arrays with the first, second and third sets of fluid reservoirs to bring all of the components of the assay (e.g., the analyte of interest, the capture probe and the magnetic label) together with the magnetic sensor array, which as described above has an analyte-specific probe bound to the surface of the sensor. The sequence and composition of the assay fluids in the sets of fluid reservoirs may be as described above, or may vary as desired. For instance, the second set of fluid reservoirs may include the magnetic label rather than the capture probe, or the third set of fluid reservoirs may include the capture probe rather than the magnetic label, or the second set of fluid reservoirs may include both the magnetic label and the capture probe. Other possible variations in the sequence and composition of the assay fluids are described in more detail below.

Embodiments of the methods are directed to determining whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular structure, sequence, and the like. In some instances, the number of analytes is greater than 2, such as 4 or more, 6 or more, 8 or more, etc., up to 20 or more, e.g., 50 or more, including 100 or more, or 1000 or more distinct analytes. In certain embodiments, the methods include the multiplex analysis of 2 to 1000 distinct analytes, such as 4 to 500 distinct analytes, including 4 to 200 distinct analytes, or 4 to 100 distinct analytes, or 4 to 50 distinct analytes, or 4 to 20 distinct analytes. In certain embodiments, several multiplex assays may be conducted in parallel substantially simultaneously. For instance, each set of fluid reservoirs on the fluid reservoir plate may have two or more analytes that are different from each other as described above, such that a multiplex assay may be performed in each fluid reservoir in the set of fluid reservoirs.

In some instances, the methods are wash-free methods of determining the presence of one or more analytes in a sample. By "wash-free" is meant that no washing step is performed following reagent and/or sample contact with a sensor surface. As such, no step is performed during the assays of these embodiments in which unbound reagent (e.g., unbound magnetic labels) or unbound sample is removed from the sensor surface. Accordingly, while the methods may include sequential contact of one or more distinct reagents and/or samples to a sensor surface, at no point during the assays is the sample surface contacted with a fluid in a manner that removes unbound reagent or sample from the sensor surface. For example, in certain embodiments, no washing step is performed following contact of the sensor surface with a sample. In some cases, the method does not include a washing step following contact of the sensor with a magnetic label. In certain instances, no washing step is performed following contact of the sensor surface with a capture probe.

In certain embodiments where a wash step is performed, the wash step does not substantially change the signal from the magnetic sensor. The wash step may not result in a substantial change in the signal from the magnetic sensor because, in some instances, unbound magnetic labels do not have a substantially detectable signal as described herein. For example, if a wash step is performed, in some cases, the wash step results in a signal change of 25% or less, such as 20% or less, or 15% or less, or 10% or less or 5% or less, or 4% or less, or 3% or less, or 2% or less, or 1% or less. In some embodiments, the wash step results in a decrease in the signal from the sensor of 25% or less, such as 20% or less, or 15% or less, or 10% or less or 5% or less, or 4% or less, or 3% or less, or 2% or less, or 1% or less.

Aspects of the methods may also include obtaining a real-time signal from the magnetic sensor device. As such, embodiments of the method include obtaining a real-time signal from the magnetic sensor arrays. By "real-time" is meant that a signal is observed as it is being produced or immediately thereafter. For example, a real-time signal is obtained from the moment of its initiation and is obtained continuously over a given period of time. Accordingly, certain embodiments include observing the evolution in real time of the signal associated with the occurrence of the binding interaction of interest (e.g., the binding of the analyte of interest to the magnetic sensor). The real-time signal may include two or more data points obtained over a given period of time, where in certain embodiments the signal obtained is a continuous set of data points (e.g., in the form of a trace) obtained continuously over a given period of time of interest. The time period of interest may vary, ranging in some instances from 0.5 min to 60 min, such as 1 min to 30 min, including 5 min to 15 min. For example, the time period may begin at the moment of initiation of the real-time signal and may continue until the sensor reaches a maximum or saturation level (e.g., where all the analyte binding sites on the sensor are occupied). The number of data points in the signal may also vary, where in some instances, the number of data points is sufficient to provide a continuous stretch of data over the time course of the real-time signal. By "continuous" is meant that data points are obtained repeatedly with a repetition rate of 1 data point per minute or more, such as 2 data points per minute or more, including 5 data points per minute or more, or 10 data points per minute or more, or 30 data points per minute or more, or 60 data points per minute or more (e.g., 1 data point per second or more), or 2 data points per second or more, or 5 data points per second or more, or 10 data points per second or more, or 20 data points per second or more, or 50 data points per second or more, or 75 data points per second or more, or 100 data points per second or more.

In certain embodiments, the real-time signal is a real-time analyte-specific signal. A real-time analyte-specific signal is a real-time signal as described above that is obtained only from the specific analyte of interest. In these embodiments, unbound analytes and unbound magnetic labels do not produce a detectable signal. As such, the real-time signal that is obtained is only from the specific magnetically-labeled analyte of interest bound to the magnetic sensor and substantially no signal is obtained from unbound magnetic labels or other reagents (e.g., analytes not specifically bound to the sensor).

In some embodiments, the signal is observed while the assay device is in a wet condition. By "wet" or "wet condition" is meant that the assay composition (e.g., an assay composition that includes a sample, a magnetic label, and a capture probe) is still in contact with the surface of the magnetic sensor. As such, there is no need to perform any washing steps to remove the non-binding moieties that are not of interest or the excess unbound magnetic labels or capture probes. In certain embodiments, the use of magnetic labels and magnetic sensors, as described above, facilitates "wet" detection because the signal induced in the magnetic sensor by the magnetic label decreases as the distance between the magnetic label and the surface of the magnetic sensor increases. For example, the use of magnetic labels and magnetic sensors, as described above, may facilitate "wet" detection because the magnetic field generated by the magnetic labels decreases as the distance between the magnetic label and the surface of the magnetic sensor increases. In some instances, the magnetic field of the magnetic label bound to the surface-bound analyte significantly exceeds the magnetic field from the unbound magnetic labels dispersed in solution. For example, as described above, a real-time analyte-specific signal may be obtained only from the specific magnetically-labeled analyte of interest bound to the magnetic sensor and substantially no signal may be obtained from unbound magnetic labels dispersed in solution (e.g., not specifically bound to the sensor). The unbound magnetic labels dispersed in solution may be at a greater distance from the surface of the magnetic sensor and may be in Brownian motion, which may reduce the ability of the unbound magnetic labels to induce a detectable change in the resistance of the magnetic sensor.

Assay Protocol

A typical assay protocol, as well as the individual components of the assay, is described in the following sections. In certain embodiments, the method includes contacting a magnetic sensor array with an assay composition that includes a sample. The magnetic sensor array may then be contacted with a magnetic label and a capture probe configured to bind to the magnetic label. A signal is obtained from the sensor to detect the presence of the analyte in the sample. Each of these steps will now be described in greater detail.

Sample

As described above, assay compositions that may be assayed in the subject methods include a sample. Samples that may be assayed in the subject methods may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure.

In certain embodiments, the samples of interest are biological samples, such as, but not limited to, urine, blood, serum, plasma, saliva, perspiration, feces, cheek swabs, cerebrospinal fluid, cell lysate samples, and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In some instances, the samples of interest are water, food or soil samples.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

Magnetic Labels

Assay compositions that may be assayed in the subject methods include a magnetic label. Magnetic labels are labeling moieties that are detectable by a sensor, such as a magnetic sensor, when the magnetic label is positioned near the sensor. While the distance between the magnetic label and sensor surface during detection may vary depending on the nature of the specific magnetic label and sensor surface, in some instances this distance ranges from 1 nm to 200 nm from the surface of the sensor, such as from 5 nm to 150 nm, including from 5 nm to 100 nm. In certain embodiments, the magnetic labels are detectable labels that are configured to specifically bind to an analyte of interest. The terms "specific binding," "specifically bind," and the like, refer to the ability of a first binding molecule or moiety (e.g., a target-specific binding moiety) to preferentially bind directly to a second binding molecule or moiety (e.g., a target molecule) relative to other molecules or moieties in a solution or reaction mixture. In certain embodiments, the affinity between a first binding molecule or moiety and a second binding molecule or moiety when they are specifically bound to each other in a binding complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

Binding of the magnetic label to the analyte of interest allows the analyte of interest to be detected by a sensor, such as a magnetic sensor, when the analyte of interest, and thus the bound magnetic label, is positioned near the sensor. In some cases, the magnetic labels are configured to bind directly to an analyte of interest. In other cases, the magnetic labels are configured to indirectly bind to an analyte of interest. For instance, a magnetic label may be configured to specifically bind to a capture probe, and the capture probe may be configured to specifically bind to the analyte of interest. Thus, binding of the magnetic label and the analyte of interest to the capture probe indirectly binds the magnetic label to the analyte of interest, e.g., to produce a labeled analyte. In some instances, the binding of the magnetic label and analyte to the capture probe is simultaneous.

In certain embodiments, the magnetic label is functionalized with one member of a binding pair. By "binding pair" or "specific binding pair" is meant two complementary binding molecules or moieties that specifically bind to each other in a binding complex. For example, a magnetic label may be functionalized with a first member of a binding pair and an analyte of interest may be functionalized with a second member of a binding pair. Thus, contacting the first and second members of the binding pair may form a binding complex between the magnetic label and the analyte of interest. In other cases, a magnetic label is functionalized with a first member of a binding pair and a capture probe is functionalized with a second member of a binding pair. Thus, contacting the first and second members of the binding pair may form a binding complex between the magnetic label and the capture probe. As described above, in some cases, the capture probe is configured to specifically bind to an analyte of interest. As such, the magnetic label may be indirectly bound to the analyte of interest through the binding complex formed between the magnetic label and the capture probe. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the magnetic label is functionalized with streptavidin and the capture probe is functionalized with biotin. As such, the magnetic label may specifically bind to the capture probe through the specific binding interaction between streptavidin and biotin. Other types of binding interactions are also possible. For example, the magnetic label may be functionalized with biotin and the capture probe may be functionalized with streptavidin. Alternatively, the magnetic label and the capture probe may be functionalized with complementary members of other specific binding pairs, as described above.

In some instances, the magnetic label is stably associated with one member of a binding pair. By "stably associated" is meant that the magnetic label and the member of the binding pair maintain their position relative to each other in space under the conditions of use, e.g., under the assay conditions. As such, the magnetic label and the member of the binding pair can be non-covalently or covalently stably associated with each other. Examples of non-covalent association include non-specific adsorption, binding based on electrostatic (e.g., ion-ion pair interactions), hydrophobic interactions, hydrogen bonding interactions, and the like. Examples of covalent binding include covalent bonds formed between the member of the binding pair and a functional group present on the surface of the magnetic label.

In certain embodiments, the magnetic labels are colloidal. The terms "colloid" or "colloidal" refer to a mixture in which one substance is dispersed throughout another substance. Colloids include two phases, a dispersed phase and a continuous phase. In some instances, colloidal magnetic labels remain dispersed in solution and do not precipitate or settle out of solution. Colloidal magnetic labels that remain dispersed in solution may facilitate a minimization in background signals and non-specific interaction of the magnetic labels with the magnetic sensor. For example, the methods may include contacting a magnetic sensor with an assay composition that includes a sample and a magnetic label, such that an analyte of interest in the sample is bound to the surface of the magnetic sensor. Because the colloidal magnetic labels remain dispersed in solution, the magnetic labels are not positioned near enough to the magnetic sensor to induce a detectable signal in the magnetic sensor, which facilitates a minimization in background signals. In some cases, specific binding of the magnetic labels to the surface-bound analyte positions the magnetic label near the magnetic sensor, such that a detectable signal is induced in the magnetic sensor.

Magnetic labels that may be employed in various methods (e.g., as described herein) may vary, and include any type of label that induces a detectable signal in a magnetic sensor when the magnetic label is positioned near the surface of the magnetic sensor. For example, magnetic labels may include, but are not limited to, magnetic labels, optical labels (e.g., surface enhanced Raman scattering (SERS) labels), fluorescent labels, and the like. Each of these types of magnetic labels is discussed in more detail below.

Magnetic labels are labeling moieties that, when sufficiently associated with a magnetic sensor, are detectable by the magnetic sensor and cause the magnetic sensor to output a signal. For example, the presence of a magnetic label near the surface of a magnetic sensor may induce a detectable change in the magnetic sensor, such as, but not limited to, a change in resistance, conductance, inductance, impedance, etc. In some cases, the presence of a magnetic label near the surface of a magnetic sensor induces a detectable change in the resistance of the magnetic sensor. Magnetic labels of interest may be sufficiently associated with a magnetic sensor if the distance between the center of the magnetic label and the surface of the sensor is 200 nm or less, such as 150 nm or less, including 100 nm or less.

In certain instances, the magnetic labels include one or more materials selected from paramagnetic, superparamagnetic, ferromagnetic, ferrimagnetic, anti-ferromagnetic materials, combinations thereof, and the like. For example, the magnetic labels may include superparamagnetic materials. In certain embodiments, the magnetic labels are configured to be nonmagnetic in the absence of an external magnetic field. By "nonmagnetic" is meant that the magnetization of a magnetic labels is zero or averages to zero over a certain period of time. In some cases, the magnetic label may be nonmagnetic due to random flipping of the magnetization of the magnetic label over time. Magnetic labels that are configured to be nonmagnetic in the absence of an external magnetic field may facilitate the dispersion of the magnetic labels in solution because nonmagnetic labels do not normally agglomerate in the absence of an external magnetic field or even in the presence of a small magnetic field in which thermal energy is still dominant. In certain embodiments, the magnetic labels include superparamagnetic materials or synthetic antiferromagnetic materials. For instance, the magnetic labels may include two or more layers of antiferromagnetically-coupled ferromagnets.

In certain embodiments, the magnetic labels are high moment magnetic labels. The magnetic moment of a magnetic label is a measure of its tendency to align with an external magnetic field. By "high moment" is meant that the magnetic labels have a greater tendency to align with an external magnetic field. Magnetic labels with a high magnetic moment may facilitate the detection of the presence of the magnetic labels near the surface of the magnetic sensor because it is easier to induce the magnetization of the magnetic labels with an external magnetic field.

In certain embodiments, the magnetic labels include, but are not limited to, Co, Co alloys, ferrites, cobalt nitride, cobalt oxide, Co—Pd, Co—Pt, iron, iron oxides, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. Examples of high moment magnetic labels include, but are not limited to, Co, Fe or CoFe nanocrystals, which may be superparamagnetic at room temperature, and synthetic antiferromagnetic nanoparticles.

In some embodiments, the surface of the magnetic label is modified. In certain instances, the magnetic labels may be coated with a layer configured to facilitate stable association of the magnetic label with one member of a binding pair, as described above. For example, the magnetic label may be coated with a layer of gold, a layer of poly-L-lysine modified glass, dextran, and the like. In certain embodiments, the magnetic labels include one or more iron oxide cores imbedded in a dextran polymer. Additionally, the surface of the magnetic label may be modified with one or more surfactants. In some cases, the surfactants facilitate an increase in the water solubility of the magnetic labels. In certain embodiments, the surface of the magnetic labels is modified with a passivation layer. The passivation layer may facilitate the chemical stability of the magnetic labels in the assay conditions. For example, the magnetic labels may be coated with a passivation layer that includes gold, iron oxide, polymers (e.g., polymethylmethacrylate films), and the like.

In certain embodiments, the magnetic labels have a spherical shape. Alternatively, the magnetic labels can be disks, rods, coils, or fibers. In some cases, the size of the magnetic labels is such that the magnetic labels do not interfere with the binding interaction of interest. For example, the magnetic labels may be comparable to the size of the analyte and the capture probe, such that the magnetic labels do not interfere with the binding of the capture probe to the analyte. In some cases, the magnetic labels are magnetic nanoparticles. In some embodiments, the average diameter of the magnetic labels is from 5 nm to 250 nm, such as from 5 nm to 150 nm, including from 10 nm to 100 nm, for example from 25 nm to 75 nm. For example, magnetic labels having an average diameter of 5 nm, 10 nm, 20 nm, 25 nm, 30 nm, 35 nm, 40 nm, 45 nm, 50 nm, 55 nm, 60 nm, 70 nm, 80 nm, 90 nm, or 100 nm, as well as magnetic labels having average diameters in ranges between any two of these values, may be used with the subject methods. In some instances, the magnetic labels have an average diameter of 50 nm.

Magnetic labels and their conjugation to biomolecules are further described in U.S. Ser. No. 12/234,506, filed Sep. 19, 2008, and entitled "Analyte Detection with Magnetic Sensors", the disclosure of which is hereby incorporated by reference in its entirety.

Assay Composition Production

In some instances, the method includes producing the assay composition by sequentially contacting the magnetic sensor array with the sample and the magnetic label. For example, the method may include contacting the magnetic sensor array first with the sample and subsequently with the magnetic label. Alternatively, the method may include contacting the magnetic sensor array first with the magnetic label and subsequently with the sample.

In other embodiments, the method includes combining the sample and the magnetic label to produce the assay composition and then contacting the magnetic sensor array with the assay composition. For instance, the method may include first combining the sample and the magnetic label in a set of fluid reservoirs to produce a set of fluid reservoirs that each contains the assay composition. Then the magnetic sensor may be contacted with the assay composition, as described above. Subsequently, the method may include contacting the magnetic sensor with the capture probe, as described in detail below.

Capture Probe

A capture probe can be any molecule that specifically binds to a protein or nucleic acid sequence that is being targeted (e.g., the analyte of interest). Depending on the nature of the analyte, capture probes can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the capture probe includes an antibody. The capture probe antibody may specifically bind to an analyte of interest. In some cases, the capture probe is a modified antibody. The modified antibody may be configured to specifically bind to the analyte of interest and may also include one or more additional members of a specific binding pair. The one or more members of a specific binding pair may be configured to specifically bind to a complementary member of the specific binding pair. In certain instances, the complementary member of the specific binding pair is bound to the magnetic label, as described above. For example, the capture probe may be an antibody that specifically binds to an analyte of interest. In addition, the capture probe may be modified to include biotin. As described above, in certain embodiments, magnetic labels may be modified to include streptavidin. As such, the capture probe may be configured to specifically bind to the analyte of interest (e.g., through an antibody-antigen interaction) and to specifically bind to the magnetic label (e.g., through a streptavidin-biotin interaction). In some cases, the capture probe is configured to bind to the analyte of interest and the magnetic label. Stated another way, the capture probe may be configured such that specific binding of the analyte to the capture probe does not significantly interfere with the ability of the capture probe to specifically bind to the magnetic label. Similarly, the capture probe may be configured such that specific binding of the magnetic label to the capture probe does not significantly interfere with the ability of the capture probe to specifically bind to the analyte.

In certain embodiments, the capture probe specifically binds to an analyte of interest. In some cases, the capture probe can be identified so that the presence of the analyte of interest can then be detected. Capture probes may be identified by any of the methods described herein. For example, as described above, analytes may be directly or indirectly bound to a magnetic sensor. The capture probe may contact and specifically bind to the analyte of interest. As indicated above, the capture probe may be configured to bind to a magnetic label and the analyte of interest. In certain instances, simultaneous binding of the capture probe to surface-bound analyte and the magnetic label positions the magnetic label within the detection range of the magnetic sensor, such that a detectable signal is induced in the magnetic sensor.

In some cases, false-positive signals due to non-specific binding of the capture probe to moieties not of interest are minimized. For example, non-specific binding of the capture probe to other moieties not of interest, which are not bound to the surface of the magnetic sensor and remain in solution, will not induce a detectable or non-negligible signal in the magnetic sensor because the magnetic label bound to the capture probe will not be positioned within the detection range of the magnetic sensor.

As described above, the magnetic label may be colloidal, such that the magnetic label remains dispersed in the assay composition solution. In certain instances, the kinetics of the capture probe diffusion to the surface of the magnetic sensor and binding to the analyte is significantly faster than the kinetics of the diffusion of the magnetic labels to the surface of the magnetic sensor. Having faster kinetics for the binding of the capture probe to the analyte than the diffusion of the magnetic label to the surface of the magnetic sensor may facilitate a minimization in false positive signals due to non-specific positioning of the magnetic label within the detection range of the magnetic sensor.

In certain embodiments, the magnetic sensor arrays are contacted with the capture probe after the magnetic sensor arrays are contacted with the assay composition. Thus, the methods may include first producing an assay composition that includes a sample and a magnetic label (e.g., in a first set of fluid reservoirs on a reservoir plate). The magnetic sensor array may then be contacted with the assay composition. Subsequently, the magnetic sensor array may be contacted with a capture probe. As described above, each component of the assay composition may be contained in sequential sets (e.g., rows) of fluid reservoirs on the reservoir plate.

Other methods are also possible. For example, the method may include first contacting the magnetic sensor arrays to the capture probe, and subsequently contacting the magnetic sensor arrays to the assay composition, where the assay composition includes a sample and a magnetic label. In both of the methods described above, the magnetic label is present in the assay composition prior to contacting the magnetic sensor array to the capture probe. In other embodiments, the sample and magnetic labels are contained in separate sets of fluid reservoirs (e.g., in separate rows of fluid reservoirs) on the reservoir plate. The magnetic sensor arrays may then be sequentially contacted with the sample, the magnetic labels and the capture probes in any desired order by sequentially positioning the magnetic sensor arrays in the corresponding sets of fluid reservoirs as desired.

As described above, in some instances, the methods are wash-free methods of determining the presence of one or more analytes in a sample. As such, in certain embodiments, contacting the magnetic sensor arrays with assay components does not include any washing steps before or after contacting the magnetic sensor arrays with each component of the assay composition. Thus, no washing step is performed either before or after the magnetic sensor is contacted with any of the assay components.

Obtaining a Signal to Determine Whether an Analyte Is Present in a Sample

Embodiments of the subject methods also include obtaining a signal from a magnetic sensor to detect the presence of an analyte in a sample. As described above, a magnetic label may be bound, either directly or indirectly, to the analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

Magnetic sensors may be configured to generate an electrical signal in response to a magnetic label in proximity to a surface of the magnetic sensor. For example, a change in the resistance of the magnetic sensor may be induced by changes in the local magnetic field. In some cases, binding of a magnetic label (e.g., a magnetic label) in close proximity to the magnetic sensor induces a detectable change in the local magnetic field of the magnetic sensor. For example, the magnetic field created by the magnetic labels that are bound to the analytes of interest may exceed the magnetic field that is created by unbound magnetic labels that remain dispersed in the sample. Changes in the local magnetic filed of the magnetic sensor may be detected as a change in the resistance of the magnetic sensor. In certain embodiments, unbound magnetic labels do not produce a detectable signal in the magnetic sensor.

Utility

The subject systems and methods find use in a variety of different applications where determination of the presence or absence, and/or quantification of one or more analytes in a sample is desired. The subject systems and methods also find use in applications where the high-throughput screening of a plurality of samples is desired. In certain embodiments, the methods are directed to detection of a set of biomarkers, e.g., two or more distinct protein biomarkers, in a plurality of samples. For example, the methods may be used in the rapid detection of two or more disease biomarkers in a group of serum samples, e.g., as may be employed in the diagnosis of a disease condition in a subject, in the ongoing management or treatment of a disease condition in a subject, etc.

In certain embodiments, the subject systems and methods find use in detecting biomarkers. In some cases, the subject systems and methods may be used to detect the presence or absence of particular biomarkers, as well as an increase or decrease in the concentration of particular biomarkers in blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject methods and systems. Furthermore, the early detection of biomarkers associated with diseases is facilitated by the picomolar and/or femtomolar sensitivity of the subject methods and systems. Due to the capability of detecting multiple biomarkers on a single magnetic sensor device, the presently disclosed assay systems and methods finds use in high-throughput screening of a plurality of samples in multiplexed molecular diagnostics.

In certain embodiments, the subject systems and methods find use in detecting biomarkers for a disease or disease state. In some cases, the disease is a cellular proliferative disease, such as but not limited to, a cancer, a tumor, a papilloma, a sarcoma, or a carcinoma, and the like. Thus, the subject systems and methods find use in detecting the presence of a disease, such as a cellular proliferative disease, such as a cancer, tumor, papilloma, sarcoma, carcinoma, or the like. In certain embodiments, the subject systems and methods find use in detecting biomarkers for an infectious disease or disease state. In some cases, the biomarkers can be molecular biomarkers, such as but not limited to proteins, nucleic acids, carbohydrates, small molecules, and the like. Similarly, the subject methods, systems and kits can be used to detect cardiovascular diseases, central nervous diseases, kidney failures, diabetes, autoimmune diseases, and many other diseases.

In certain embodiments, the subject methods, systems and kits can be used to detect the presence or absence, and/or quantification of one or more analytes in a plurality of samples for food and/or environmental safety. For example, the subject systems and methods can be used to determine the presence of analytes in a plurality of samples of potentially contaminated water, soil or food, such as for the detection of infectious disease agents, e.g., bacteria, viruses, molds, etc., including potential biological warfare agents.

Computer Related Embodiments

A variety of computer-related embodiments are also provided. Specifically, the data analysis methods described in the previous sections may be performed using a computer. Accordingly, provided is a computer-based system for analyzing data produced using the above methods in order to provide qualitative and/or quantitative determination of a binding interaction of interest.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, DVD-ROM, BD-ROM, a hard disk drive, a ROM or integrated circuit, a magneto-optical disk, a solid-state memory device, a computer readable card such as a PCMCIA card, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media does not include electronic signals in transit via a wireless protocol.

With respect to computer readable media, "permanent memory" refers to memory that is permanent. Permanent memory is not erased by termination of the electrical supply to a computer or processor. Computer hard-drive, CD-ROM, DVD-ROM, BD-ROM, and floppy disk are all examples of permanent memory. Random Access Memory (RAM) is an example of non-permanent memory. A file in permanent memory may be editable and re-writable.

Kits

Also provided are kits for practicing one or more embodiments of the above-described methods. The subject kits may vary, and may include various devices and reagents. Reagents and devices include those mentioned herein with respect to magnetic sensor devices or components thereof (such as a magnetic sensor array), magnetic labels, capture probes, analyte-specific probes, buffers, etc. The reagents, magnetic labels, capture probes, etc. may be provided in separate containers, such that the reagents, magnetic labels, capture probes, etc. may be used individually as desired. Alternatively, one or more reagents, magnetic labels, capture probes, etc. may be provided in the same container such that the one or more reagents, magnetic labels, capture probes, etc. is provided to a user pre-combined.

In certain embodiments, the kits include a magnetic sensor device as described above, and a magnetic label. For example, the magnetic label may be a magnetic nanoparticle, as described above. In certain embodiments, the kits include a reservoir plate that has a plurality of fluid reservoirs as described above.

In some instances, the kits include at least reagents finding use in the methods (e.g., as described above); and a computer readable medium having a computer program stored thereon, wherein the computer program, when loaded into a computer, operates the computer to qualitatively and/or quantitatively determine a binding interaction of interest from a real-time signal obtained from a magnetic sensor; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, etc., on which the information has been recorded. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

An experiment was performed to test a high-throughput magnetic sensor system according to embodiments of the present disclosure. The magnetic sensor arrays were prepared with two types of surface chemistry, one which adsorbs magnetic nanoparticles (e.g., positive sensors), and one which does not adsorb magnetic nanoparticles (e.g., control sensors). One-half of the sensors in each array were positive sensors.

The magnetic sensor device was stationary in the magnetically active region inside the magnetic field source (e.g., the magnetic coil). The reservoir plate with the fluid reservoirs was lifted up to be engaged in an operative relationship with the magnetic sensor arrays, and lowered to be disengaged from the operative relationship and advanced from one row of fluid reservoirs to the next row of fluid reservoirs.

In a typical experiment, the signal level increase of the positive sensors is a measure of the concentration of an analyte present in the solution. In this example, the signal level increase was a measure of the concentration of magnetic nanoparticles in the sample solution.

Figure 3:
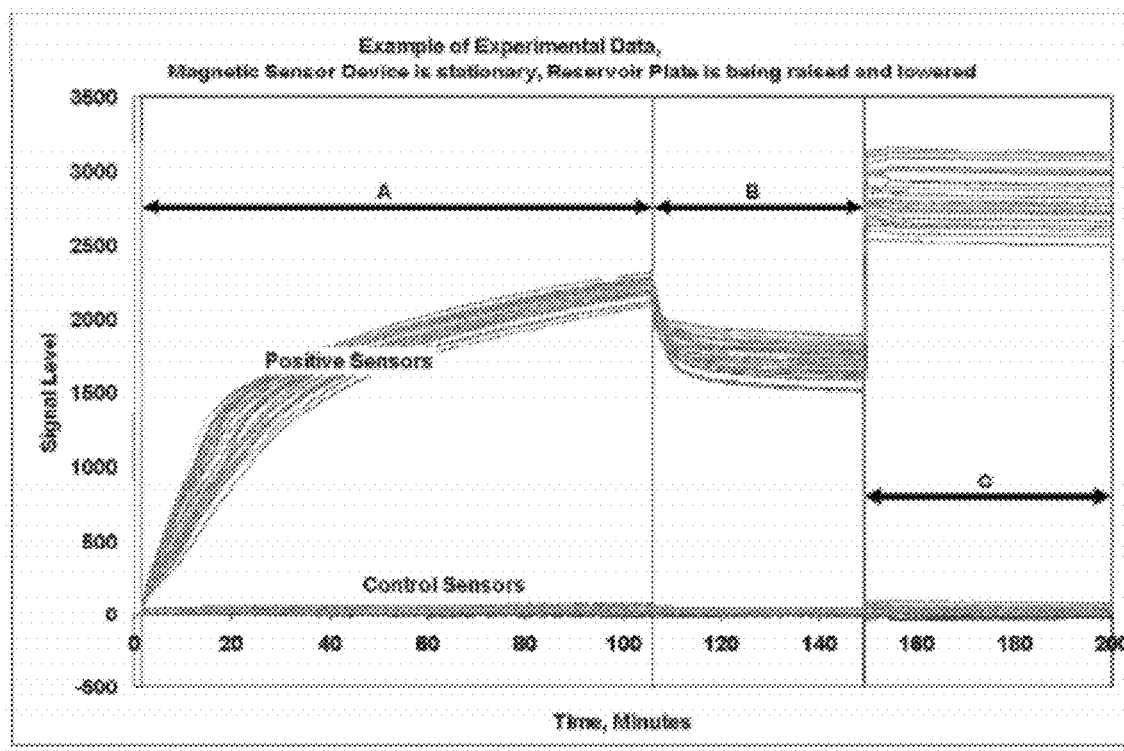
FIG. 3 shows a graph of signal level over time for a high-throughput magnetic biosensor system according to embodiments of the present disclosure.

FIG. 3 shows a graph of the signal level from the magnetic sensor arrays on the magnetic sensor device over time (minutes). The graph shows the signal level from positive sensors and control sensors in the magnetic sensor arrays. As shown in FIG. 3, in Region A of the graph, the signal level increased on the positive sensors when the magnetic sensor arrays were engaged with the fluid reservoirs containing a magnetic nanoparticle solution. This was the result of magnetic nanoparticles being adsorbed onto the positive sensors. In Region B of the graph, the signal partially decreased when the magnetic sensor arrays were engaged to fluid reservoirs containing deionized water. This was the result of some magnetic nanoparticles being removed from the sensor array. As shown in Region C, the signal level was stable as the magnetic sensor arrays dried after being disengaged from the fluid reservoirs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A high-throughput detection system comprising:
(a) a magnetic sensor device comprising a support with two or more elongated regions each having a magnetic sensor array comprising one or more magnetic sensor selected from the group consisting of a spin valve detector and a magnetic tunnel junction detector disposed at a distal end of the elongated region, wherein one or more magnetic sensor has an analyte-specific probe bound to a surface of the magnetic sensor;
(b) a magnetic field source; and
(c) a reservoir plate comprising sequential sets of a plurality of fluid reservoirs,
wherein the system is configured to position the magnetic sensor arrays in the sequential sets of the fluid reservoirs.

2. The system of claim 1, wherein each magnetic sensor array comprises one or more magnetic sensors having an analyte-specific probe bound to a surface of the magnetic sensor.

3. The system of claim 1, further comprising a first reservoir plate actuator configured to move the reservoir plate into an operative relationship with the magnetic sensor device such that the distal ends of the elongated regions of the magnetic sensor device are each positioned in separate fluid reservoirs.

4. The system of claim 3, further comprising a second reservoir plate actuator configured to move the reservoir plate along at least one axis coplanar with the reservoir plate.

5. The system of claim 1, further comprising a magnetic sensor device actuator configured to move the magnetic sensor device into an operative relationship with the magnetic field source.

6. The system of claim 1, further comprising a processor configured to obtain a real-time analyte-specific signal from the magnetic sensor array.

7. The system of claim 1, further comprising a processor configured to obtain a real-time analyte-specific signal from the magnetic sensor array as a magnetically-labeled analyte in a sample binds to an analyte-specific probe or as a magnetic label binds to an analyte/analyte-specific probe complex.

8. A high-throughput detection system comprising:
 (a) a magnetic field source;
 (b) a first reservoir plate actuator configured to position a reservoir plate having sequential sets of a plurality of fluid reservoirs into an operative relationship with a magnetic sensor device; and
 (c) the magnetic sensor device, wherein the magnetic sensor device comprises a support with two or more elongated regions each having a magnetic sensor array comprising one or more magnetic sensor selected from the group consisting of a spin valve detector and a magnetic tunnel junction detector disposed at a distal end of the elongated regions, wherein one or more magnetic sensor has an analyte-specific probe bound to a surface of the magnetic sensor,
 wherein the system is configured to position the two or more magnetic sensor arrays in the sequential sets of the fluid reservoirs.

9. The system of claim 8, further comprising a second reservoir plate actuator configured to move the reservoir plate along at least one axis coplanar with the reservoir plate.

10. The system of claim 8, further comprising a magnetic sensor device actuator configured to move the magnetic sensor device into an operative relationship with the magnetic field source.

11. The system of claim 8, further comprising a processor configured to obtain a real-time analyte-specific signal from the magnetic sensor arrays.

12. A magnetic sensor device comprising:
 a support with two or more elongated regions each having a magnetic sensor array comprising one or more magnetic sensor selected from the group consisting of a spin valve detector and a magnetic tunnel junction detector disposed at a distal end of the elongated region, wherein one or more magnetic sensor has an analyte-specific probe bound to a surface of the magnetic sensor.

13. The device of claim 12, wherein each magnetic sensor array comprises two or more magnetic sensors having an analyte-specific probe bound to a surface of the magnetic sensor.

14. The device of claim 12, wherein each distal end of the elongated regions is sized to fit within separate fluid reservoirs.

15. The device of claim 13, wherein at least one of the magnetic sensor arrays comprises two or more distinct magnetic sensors each configured to specifically detect the same analyte.

16. The device of claim 13, wherein at least one of the magnetic sensor arrays comprises two or more distinct magnetic sensors each configured to specifically detect a different analyte.

17. The device of claim 13, wherein at least two of the magnetic sensor arrays comprise distinct magnetic sensors and are configured to specifically detect a different set of analytes.

18. The system of claim 1, wherein the magnetic field source comprises two or more magnetic field sources positioned on opposite sides of the reservoir plate.

19. The system of claim 1, further comprising a signal socket configured to connect to and receive signals from the magnetic sensor device.

* * * * *

UNITED STATES PATENT AND TRADEMARK OFFICE
CERTIFICATE OF CORRECTION

| | | |
|---|---|---|
| PATENT NO. | : 9,151,763 B2 | Page 1 of 1 |
| APPLICATION NO. | : 13/416928 | |
| DATED | : October 6, 2015 | |
| INVENTOR(S) | : Osterfeld et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twenty-fourth Day of May, 2016

Michelle K. Lee
*Director of the United States Patent and Trademark Office*